United States Patent [19]
Tamaoki et al.

[11] Patent Number: 5,674,867
[45] Date of Patent: Oct. 7, 1997

[54] INDOLOCARBAZOLE DERIVATIVES AND THERAPEUTIC METHOD FOR STIMULATING MEGAKAICYOCYTE PRODUCTION

[75] Inventors: Tatsuya Tamaoki, Machida; Yukimasa Shiotsu, Tokyo; Chikara Murakata, Hachioji; Shiro Akinaga, Sunto-gun; Masami Okabe, Mishima; Yutaka Saito, Machida; Junichi Watanabe, Machida; Takako Shiraki, Machida, all of Japan

[73] Assignee: Kyowa Hakko Kogyo Co., Ltd., Tokyo, Japan

[21] Appl. No.: 244,111

[22] PCT Filed: Sep. 20, 1993

[86] PCT No.: PCT/JP93/01346

§ 371 Date: May 18, 1994

§ 102(e) Date: May 18, 1994

[87] PCT Pub. No.: WO94/06799

PCT Pub. Date: Mar. 3, 1994

[30] Foreign Application Priority Data

Sep. 21, 1992 [JP] Japan .................... 4-250941

[51] Int. Cl.$^6$ .................... A61K 31/55; C07D 498/22
[52] U.S. Cl. .................... 514/219; 514/255; 514/410; 540/545; 540/546; 540/543; 544/359; 544/372; 544/416
[58] Field of Search .................... 540/545, 546, 540/543; 544/359, 372; 548/416; 514/219, 255, 410

[56] References Cited

U.S. PATENT DOCUMENTS

| | | | |
|---|---|---|---|
| 4,107,297 | 8/1978 | Omura et al. | 424/122 |
| 4,555,402 | 11/1985 | Matsuda et al. | 424/122 |
| 4,877,776 | 10/1989 | Murakata et al. | 514/43 |
| 4,923,986 | 5/1990 | Murakata et al. | 540/545 |
| 4,935,415 | 6/1990 | Nakano et al. | 514/211 |
| 5,093,330 | 3/1992 | Caravatti et al. | 514/211 |

FOREIGN PATENT DOCUMENTS

| | | |
|---|---|---|
| 0617324 | 12/1988 | Australia . |
| 0296110 | 12/1988 | European Pat. Off. . |
| 0383919 | 8/1990 | European Pat. Off. . |
| 0575955 | 12/1993 | European Pat. Off. . |
| 0155284 | 7/1987 | Japan . |
| 0295588 | 12/1988 | Japan . |
| 0295589 | 12/1988 | Japan . |
| 0120388 | 6/1989 | Japan . |
| 0072485 | 3/1991 | Japan . |
| 0220194 | 9/1991 | Japan . |
| 9307153 | 4/1993 | WIPO . |

OTHER PUBLICATIONS

Furuski et al. J. Chem. Soc. Chem. Comm. pp. 800–801, 1978.
Yamada et al. Chemical Abstract. CA:117:234461, 1992.
Murakata et al. Chemical Abstract. CA:112:77240, 1989.
The Journal of Antibiotics, vol. XXXVIII, No. 10 (Oct. 1985) 1437–39.
The Journal of Antibiotics, vol. XXXIX, No. 8 (Aug. 1986) 1066–71.
Honma et al., Cancer Research, vol. 51, No. 17 (Sep. 1991) 4649–55.
Del Zoppo, Seminars in Hematology, vol. 24, No. 2 (1987) 130–39.
Chemical Abstracts, vol. 116, No. 7 (Feb. 1992) 59419k.
Derwent Patent Abstract JP 4–145085, 1992.

*Primary Examiner*—Yogendra N. Gupta
*Attorney, Agent, or Firm*—Fitzpatrick, Cella, Harper & Scinto

[57] ABSTRACT

The present invention relates to therapeutic agents for thrombocytopenia which contain an indolocarbazole derivative represented by the formula (I) given below or a pharmaceutically acceptable salt thereof as an active ingredient, and to novel indolocarbazole derivatives.

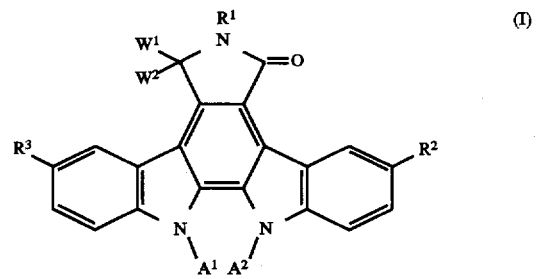

3 Claims, No Drawings

INDOLOCARBAZOLE DERIVATIVES AND THERAPEUTIC METHOD FOR STIMULATING MEGAKAICYOCYTE PRODUCTION

This application is a 371 of PCT/JP93/01346 filed on Sep. 20, 1997.

TECHNICAL FIELD

The present invention relates to a therapeutic agent for thrombocytopenia and novel indolocarbazole derivatives. Therapeutic agents for thrombocytopenia are expected to be useful for the treatment of the decrease in the number of blood platelets which is a side effect of chemotherapy for cancer and transplantation of bone marrow and for various diseases involving thrombocytopenia.

BACKGROUND ART

The decrease in the number of blood platelets due to various kinds of hematopoietic disorders causes grave symptoms including an increased tendency to hemorrhage. At present, platelet transfusion is employed as an effective means for the treatment of such decrease, but it does not always enable a sufficient supply of blood platelets.

Known hematopoietic factors which stimulate the production of blood platelets include interleukin (IL) 6 and IL 11.

Indolocarbazole derivatives are known to have inhibitory activity against a variety of protein kinase, including protein kinase C, antibacterial activity, and anti-tumor activity [Japanese Published Unexamined Patent Application No. 155284/87, Japanese Published Unexamined Patent Application No. 220196/87 (EP-A-238011), Japanese Published Unexamined Patent Application No. 295588/88, Japanese Published Unexamined Patent Application No. 295589/88, Japanese Published Unexamined Patent Application No. 168689/89 (EP-A-323171), WO 88-07045 (U.S. Pat. No. 4,923,986), WO 89-07105 (EP-A-383919)].

DISCLOSURE OF THE INVENTION

According to the present invention, there is provided a therapeutic agent for thrombocytopenia which contains an indolocarbazole derivative represented by the following general formula (I) (hereinafter abbreviated to Compound I) or a pharmaceutically acceptable salt thereof as an active ingredient.

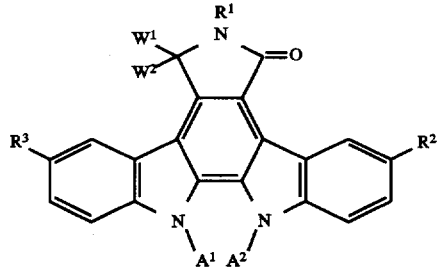

[In the formula, $R^1$ represents hydrogen, lower alkyl, lower alkanoyl, benzyl or amino; $R^2$ represents hydrogen, hydroxy, lower alkoxy, lower alkanoyl, halogen or the formula (i):

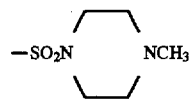

$R^3$ represents hydrogen, lower alkanoyl, halogen, hydroxy or lower alkoxy; one of $W^1$ and $W^2$ is hydrogen, and the other is hydrogen, hydroxy or lower alkylthio, or $W^1$ and $W^2$ are combined together to represent oxygen; and $A^1$ and $A^2$ are the same and are hydrogen, or $A^1$ and $A^2$ are combined together to represent the formula (ii):

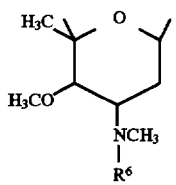

(wherein $R^6$ is hydrogen, benzyloxycarbonyl, lower alkyl or lower alkanoyl), or the formula (iii):

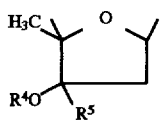

(wherein $R^4$ is hydrogen, lower alkyl, methoxymethyl or lower alkanoyl; and $R^5$ is hydrogen or lower alkoxycarbonyl).]

The therapeutic agent according to the present invention is effective in increasing the reduced number of blood platelets.

In the definitions of the groups in Compound I, the lower alkyl means a straight-chain or branched alkyl group having 1–6 carbon atoms, such as methyl, ethyl, propyl, isopropyl, butyl, isobutyl, sec-butyl, tert-butyl, pentyl, neopentyl, and hexyl.

The alkyl moiety of the lower alkoxy, lower alkoxycarbonyl and lower alkylthio has the same definition as the lower alkyl mentioned above.

The lower alkanoyl means an alkanoyl group having 1–7 carbon atoms, such as formyl, acetyl, propionyl, isopropionyl, butyryl, valeryl, pivaloyl, hexanoyl, and heptanoyl.

The pharmaceutically acceptable salts of Compound I include salts with inorganic acids such as hydrochloride, sulfate, and phosphate, and salts with organic acids such as acetate, maleate, fumarate, tartrate, citrate, lactate, aspartate, and glutamate.

Examples of Compound I are listed in Table 1.

In the table, n-Pr stands for —$(CH_2)_2CH_3$, i-Pr stands for —$CH(CH_3)_2$, n-Bu stands for —$(CH_2)_3CH_3$, n-Hex stands for —$(CH_2)_5CH_3$, and Bn stands for benzyl.

\* Compound I-4 is a mixture of a stereoisomer wherein $W^1$=H and $W^2$=OH and a stereoisomer wherein $W^1$=OH and $W^2$=H, and Compound I-14 is a mixture of a stereoisomer wherein $W^1$=H and $W^2$=—$SCH_2CH_3$, and a stereoisomer wherein $W^1$=—$SCH_2CH_3$ and $W^2$=H.

TABLE 1

| Compound No. | R¹ | R² | R³ | W¹ | W² | A¹ | A² | Salt |
|---|---|---|---|---|---|---|---|---|
| I-1 | H | H | H | H | OH | (structure: tetrahydropyran with H₃C, H₃CO, NH-CH₃ substituents) | | |
| I-2 | CH₃ | H | H | H | H | (structure: tetrahydropyran with H₃C, H₃CO, NH-CH₃ substituents) | | HCl |
| I-3 | NH₂ | H | H | combined to represent O | | (structure: tetrahydropyran with H₃C, H₃CO, NH-CH₃ substituents) | | HCl |
| I-4 | H | H | H | H | OH | (structure: tetrahydrofuran with H₃C, HO, CO₂CH₃ substituents) | | |
| I-5 | H | H | H | H | H | (structure: tetrahydrofuran with H₃C, HO, CO₂(CH₂)₅CH₃ substituents) | | |
| I-6 | H | O-n-Pr | H | H | H | (structure: tetrahydrofuran with H₃C, HO, CO₂CH₃ substituents) | | |
| I-7 | CH₃ | H | H | H | H | (structure: tetrahydrofuran with H₃C, H₃CO, CO₂CH₃ substituents) | | |
| I-8 | CH₃CO | H | H | H | H | (structure: tetrahydrofuran with H₃C, H₃COCO, CO₂CH₃ substituents) | | |
| I-9 | CH₃ | H | H | combined to represent O | | (structure: tetrahydropyran with H₃C, H₃CO, NH-CH₃ substituents) | | HCl |
| I-10 | H | O-n-Bu | H | H | H | (structure: tetrahydrofuran with H₃C, HO, CO₂CH₃ substituents) | | |
| I-11 | H | -SO₂-N(piperazinyl)N-CH₃ | H | H | H | (structure: tetrahydrofuran with H₃C, HO, CO₂CH₃ substituents) | | |

TABLE 1-continued

| Compound No. | R¹ | R² | R³ | W¹ | W² | A¹ | A² | Salt |
|---|---|---|---|---|---|---|---|---|
| I-12 | H | O-n-Pr | O-n-Pr | H | H | tetrahydropyran with H₃C–, HO–, –CO₂CH₃ substituents | | |
| I-13 | Bn | H | H | combined to represent O | | tetrahydropyran with H₃C–, HO–, –CO₂CH₃ substituents | | |
| I-14 | H | H | H | H | SCH₂CH₃ | tetrahydropyran with H₃C–, HO–, –CO₂CH₃ substituents | | |
| I-15 | H | H | H | H | H | tetrahydropyran with H₃C–, HO–, –CO₂-n-Bu substituents | | |
| I-16 | H | H | H | H | H | H | H | |
| I-17 | H | H | H | H | H | tetrahydropyran with H₃C–, H₃CO–, –NH–CH₃ substituents | | |
| I-18 | CH₃ | H | H | H | H | tetrahydropyran with H₃C–, H₃CO–, –N(CH₃)(CO₂–Bn) substituents | | |
| I-19 | n-Pr | H | H | H | H | tetrahydropyran with H₃C–, H₃CO–, –NH–CH₃ substituents | | HCl |
| I-20 | n-Hex | H | H | H | H | tetrahydropyran with H₃C–, H₃CO–, –NH–CH₃ substituents | | HCl |
| I-21 | Bn | H | H | H | H | tetrahydropyran with H₃C–, H₃CO–, –NH–CH₃ substituents | | HBr |

TABLE 1-continued

| Compound No. | R¹ | R² | R³ | W¹ | W² | A¹ | A² | Salt |
|---|---|---|---|---|---|---|---|---|
| I-22 | CH₃ | H | H | H | H | | H₃C, H₃CO, N(H)(CH₃) pyranyl | Asp |
| I-23a | CH₃ | H | H | H | OH | | H₃C, H₃CO, N(H)(CH₃) pyranyl | |
| I-23b | CH₃ | H | H | H | OH | | H₃C, H₃CO, N(H)(CH₃) pyranyl | |
| I-24 | CH₃ | H | H | H | H | | H₃C, H₃CO, N(n-Pr)(CH₃) pyranyl | |
| I-25 | H | H | H | H | H | | H₃C, H₃CO, N(H)(CH₃) pyranyl | |
| I-26 | H | H | H | H | H | | H₃C, H₃CO, N(n-Pr)(CH₃) pyranyl | |
| I-27 | H | H | H | H | H | | H₃C, H₃CO, N(n-Hex)(CH₃) pyranyl | |
| I-28 | H | H | H | H | H | | H₃C, H₃CO, N(COCH₃)(CH₃) pyranyl | |

TABLE 1-continued

| Compound No. | R¹ | R² | R³ | W¹ | W² | A¹ | A² | Salt |
|---|---|---|---|---|---|---|---|---|
| I-29 | H | Br | H | H | H | (structure with H₃C, H₃CO, N—CH₃, H on tetrahydropyran) | | |
| I-30 | H | COCH₃ | H | H | H | (structure with H₃C, H₃CO, N—CH₃, H on tetrahydropyran) | | |
| I-31 | H | COCH₃ | COCH₃ | H | H | (structure with H₃C, H₃CO, N—CH₃, H on tetrahydropyran) | | |
| I-32 | H | CHO | CHO | H | H | (structure with H₃C, H₃CO, N—CH₃, H on tetrahydropyran) | | |
| I-33 | H | O-n-Pr | H | H | H | (structure with H₃C, H₃CO, N—CH₃, H on tetrahydropyran) | | |
| I-34 | CH | H | H | H | H | (structure with H₃C, H₃CO, N—CH₃, H on tetrahydropyran) | | |
| I-35 | H | H | H | H | H | (structure with H₃C, HO, CO₂CH₃ on tetrahydrofuran) | | |
| I-36 | H | H | H | H | H | (structure with H₃C, HO, CO₂CH₃ on tetrahydrofuran) | | |
| I-37 | COCH₃ | COCH₃ | H | H | H | (structure with H₃C, H₃CCOO, CO₂CH₃ on tetrahydrofuran) | | |

TABLE 1-continued

| Compound No. | R¹ | R² | R³ | W¹ | W² | A¹ | A² | Salt |
|---|---|---|---|---|---|---|---|---|
| I-38 | CH₃ | O-n-Pr | H | H | H | | $H_3C-,HO-,CO_2CH_3$ tetrahydrofuran | |
| I-39 | H | H | H | H | H | | $H_3C-,H_3COCH_2O-,CO_2CH_3$ | |
| I-40 | H | Br | Br | H | H | | $H_3C-,HO-,CO_2CH_3$ | |
| I-42 | H | H | H | H | H | | $H_3C-,HO-,CO_2\text{-}n\text{-}Pr$ | |
| I-43 | H | H | H | combined to represent O | | | $H_3C-,HO-,CO_2\text{-}n\text{-}Bu$ | |
| I-44 | n-Pr | H | H | combined to represent O | | | $H_3C-,HO-,CO_2CH_3$ | |
| I-45 | H | H | H | H | H | | $H_3C-,HO-,CO_2\text{-}i\text{-}Pr$ | |
| I-46 | H | H | H | H | H | | $H_3C-,HO-,H$ | |
| I-47 | CH₃ | OH | H | H | H | | $H_3C-,H_3CO-,NH\text{-}CH_3$ (piperidine) | HCl |
| I-48 | CH₃ | OH | OH | H | H | | $H_3C-,H_3CO-,NH\text{-}CH_3$ (piperidine) | HCl |

TABLE 1-continued

| Compound No. | R¹ | R² | R³ | W¹ | W² | A¹ | A² | Salt |
|---|---|---|---|---|---|---|---|---|
| I-49 | CH₃ | H | H | H | H | (structure) | | HCl |
| I-50 | CH₃ | CHO | H | H | H | (structure) | | |
| I-51 | CH₃ | COCH₃ | COCH₃ | H | H | (structure) | | |
| I-52 | H | OH | H | H | H | (structure) | | |

The present invention also provides indolocarbazole derivatives represented by the formulae (II) and (III) and pharmaceutically acceptable salts thereof.

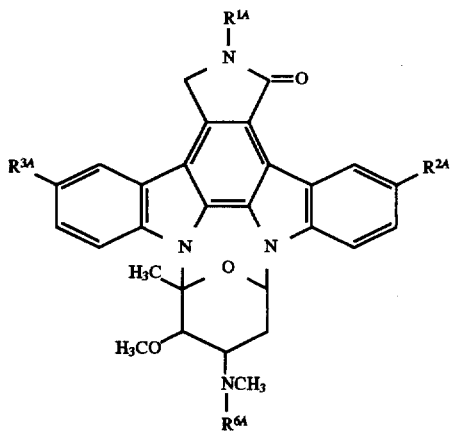

(II)

[In the formula,
(a) $R^{1A}$ is hexyl, and $R^{2A}$, $R^{3A}$ and $R^{6A}$ are hydrogen;
(b) $R^{1A}$ is benzyl, and $R^{2A}$, $R^{3A}$ and $R^{6A}$ are hydrogen;
(c) $R^{1A}$ is methyl, $R^{2A}$ and $R^{3A}$ are hydrogen, and $R^{6A}$ is lower alkyl;
(d) $R^{1A}$ is hydrogen or lower alkyl, $R^{3A}$ and $R^{6A}$ are hydrogen, and $R^{2A}$ is halogen or lower alkanoyl;
(e) $R^{1A}$ is hydrogen or lower alkyl, $R^{6A}$ is hydrogen, and $R^{2A}$ and $R^{3A}$ are lower alkanoyl;
(f) $R^{1A}$, $R^{3A}$ and $R^{6A}$ are hydrogen, and $R^{2A}$ is lower alkoxy; or
(g) $R^{1A}$ is lower alkyl, $R^{6A}$ is hydrogen, $R^{2A}$ is hydroxy, and $R^{3A}$ is hydroxy or hydrogen.]

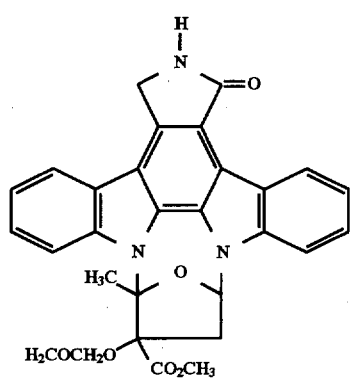

(III)

Examples of the compounds represented by the general formula (II) include Compounds I-20, I-21, I-24, I-29, I-30, I-31, I-32, I-33, I-39, I-47, I-48, I-49, I-50 and I-51.

The processes for the production of the above novel compounds are described below.

(1) Compound (Ia) [Compound I in which R¹ is hexyl or benzyl]

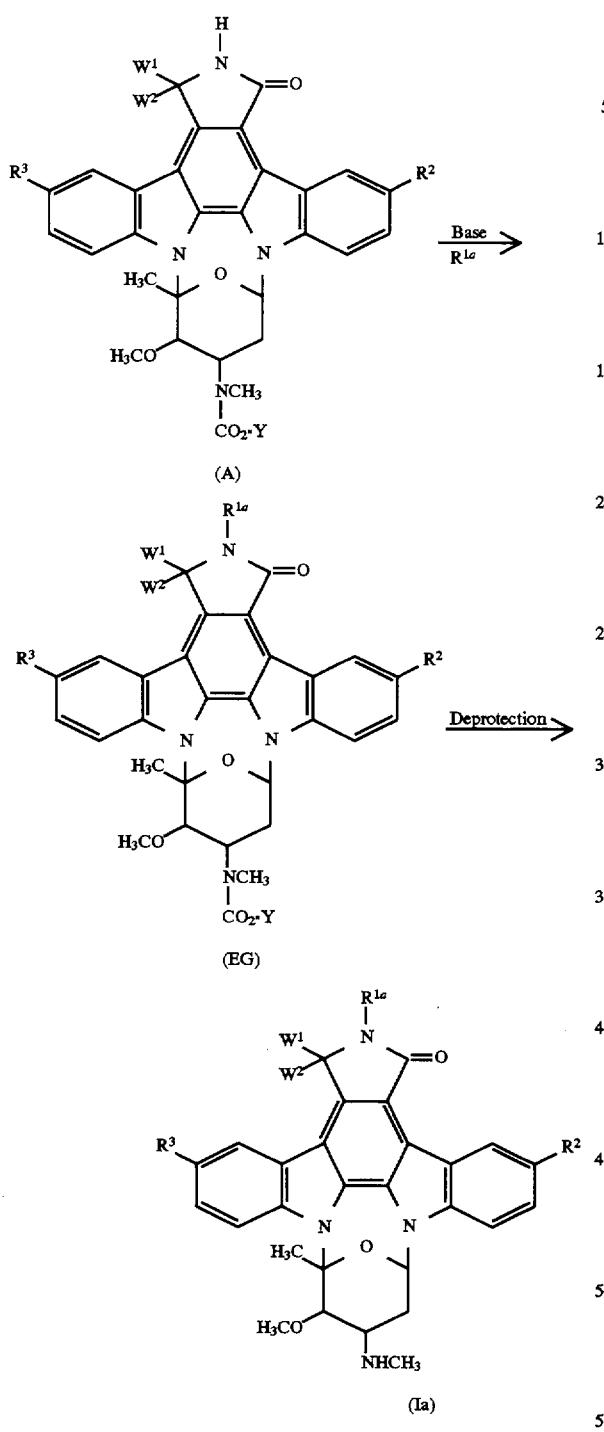

(A)

(EG)

(Ia)

(In the formulae, $R^{1a}$ represents hexyl or benzyl; Y represents benzyl or tert-butyl; X represents I, Br or Cl; and $W^1$, $W^2$, $R^2$ and $R^3$ have the same meanings as defined above.)

Compound (A) is allowed to react with $R^{1a}X$ in the presence of a base such as sodium hydride in an appropriate solvent such as dimethylformamide (DMF) to give Compound (EG). Sodium hydride and $R^{1a}X$ are used in amounts of 1 to 5 equivalents based on Compound (A). The reaction is carried out at $-23°$ to $30°$ C. and is completed in 1 to 8 hours.

Then, Compound (EG) wherein Y is benzyl is subjected to deprotection in a hydrogen stream, in the presence of a catalyst such as 10% Pd/C or 10% Pd(OH)$_2$/C, in an appropriate solvent such as DMF to give Compound (Ia). The amount of the catalyst to be used is 0.1 to 2 times that of Compound (EG) by weight. The reaction is carried out at $0°$ to $80°$ C. and is completed in 1 to 8 hours.

On the other hand, the compound wherein Y is tert-butyl is deprotected in the presence of an appropriate acid such as hydrobromic acid/acetic acid in an appropriate solvent such as chloroform to give Compound (Ia). The reaction is carried out at $0°$ to $50°$ C. and is completed in one hour.

(2) Compound (Ib) [Compound I in which $R^6$ is lower alkyl]

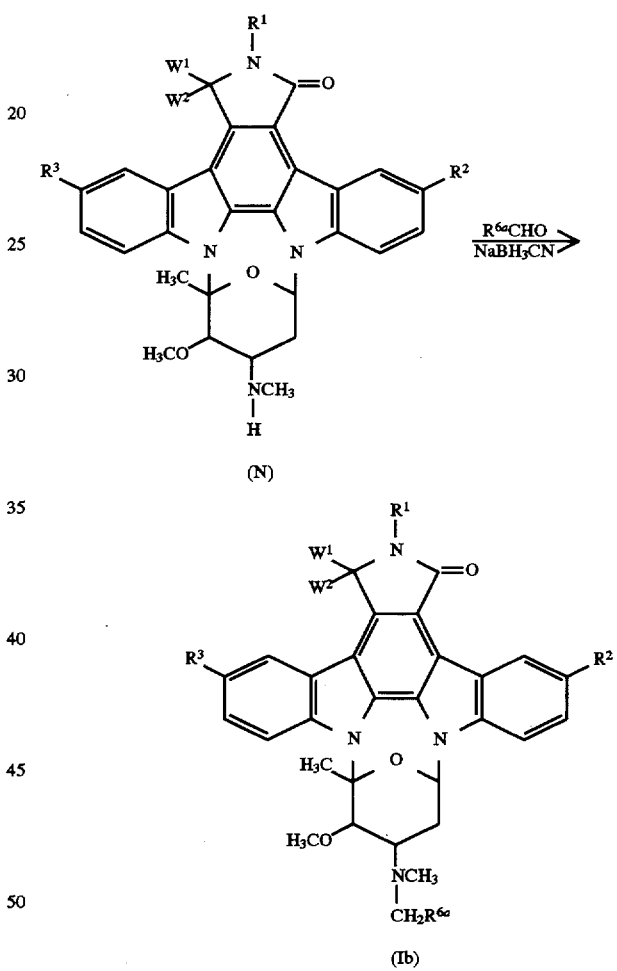

(N)

(Ib)

(In the formulae, $R^{6a}$ represents hydrogen or $C_{1-5}$ lower alkyl; and $R^1$, $R^2$, $R^3$, $W^1$ and $W^2$ have the same meanings as defined above.)

Compound (N) is allowed to react with $R^{6a}CHO$ in the presence of a reducing agent such as sodium cyanoborohydride in an appropriate solvent such as tetrahydrofuran (THF) to give Compound (Ib). The reducing agent and $R^{6a}CHO$ are used in amounts of 1 to 2 equivalents and 1 to 5 equivalents, respectively, based on Compound (N). The reaction is carried out at $0°$ to $30°$ C. and is completed in 1 to 5 hours.

(3) Compound (Ic) [Compound I in which $R^2$ is halogen]

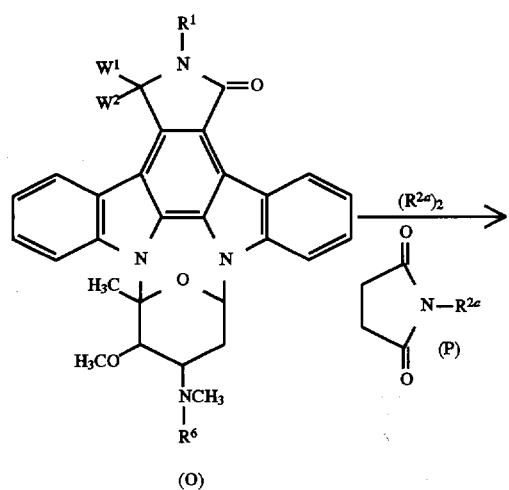

(O)

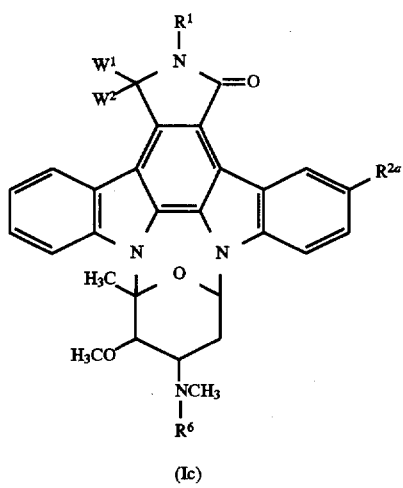

(Ic)

(In the formulae, $R^{2a}$ represents Cl or Br; and $R^1$, $R^6$, $W^1$ and $W^2$ have the same meanings as defined above.)

Compound (O) is allowed to react with a halogen or Compound (P) in an appropriate solvent such as chloroform to give Compound (Ic). The halogen or Compound (P) is used in an amount of 0.8 to 1.5 equivalents based on Compound (O). The reaction is completed in 1 to 8 hours.

(4) Compound (Id) [Compound I in which $R^2$ is alkanoyl of 2–7 carbon atoms, and $R^3$ is hydrogen or alkanoyl of 2–7 carbon atoms]

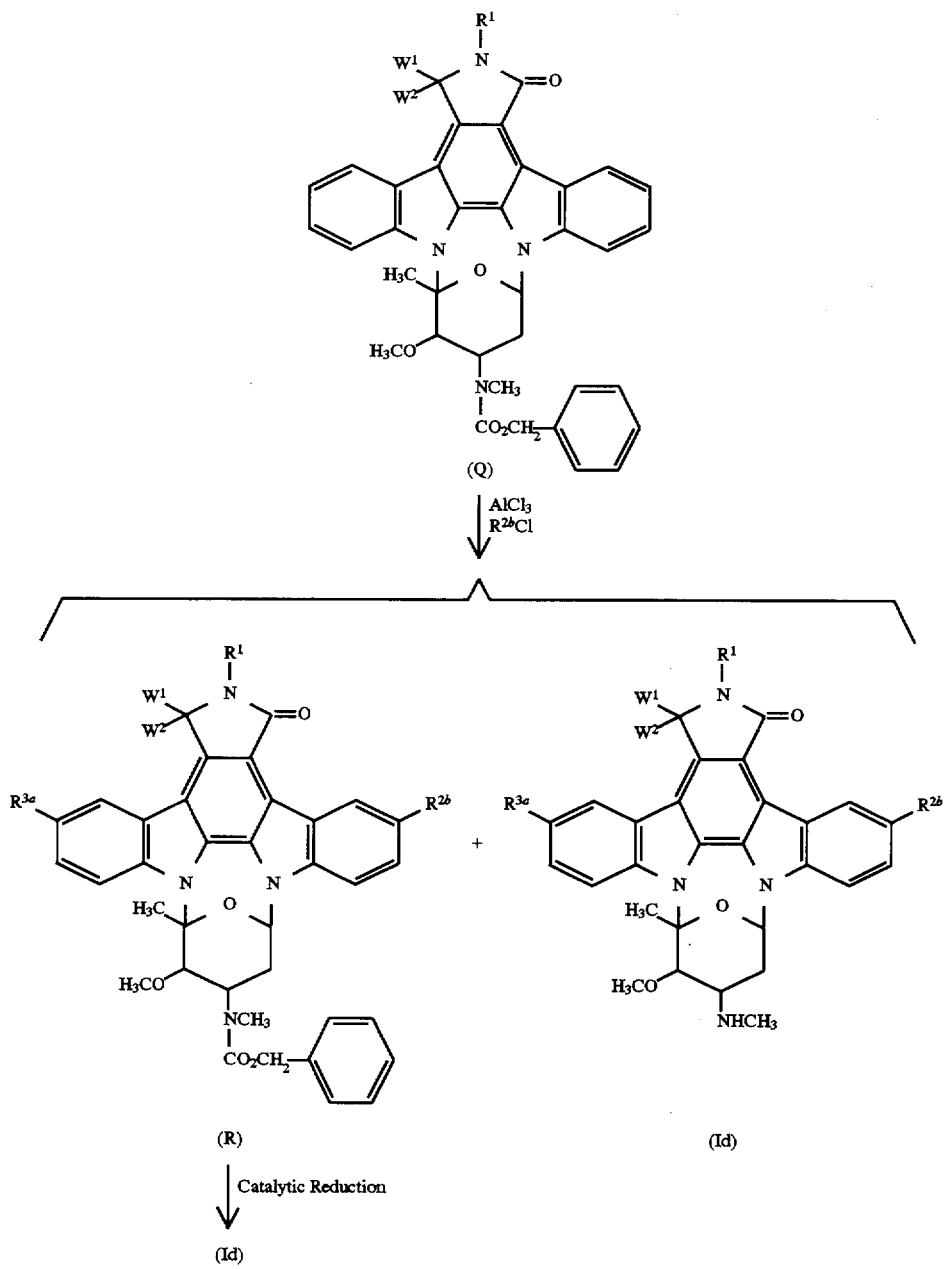

(In the formulae, $R^{2b}$ represents alkanoyl of 2–7 carbon atoms; $R^{3a}$ represents hydrogen or $R^{2b}$; and $R^1$, $W^1$ and $W^2$ have the same meanings as defined above.)

Compound (Q) is allowed to react with an alkanoyl chloride in the presence of an appropriate Lewis acid such as aluminum chloride in an appropriate solvent such as dichloromethane to give Compound (R) and Compound (Id). The alkanoyl chloride and the Lewis acid are used in amounts of 1 to 8 equivalents based on Compound (Q). The reaction is carried out at $-10°$ to $30°$ C. and is completed in 1 to 8 hours.

Compound (Id) may also be obtained by catalytic reduction of Compound (R) in the same manner as in the case of Compound (Ia).

(5) Compound (Ie) [Compound I in which $R^2$ is formyl, and $R^3$ is hydrogen or formyl]

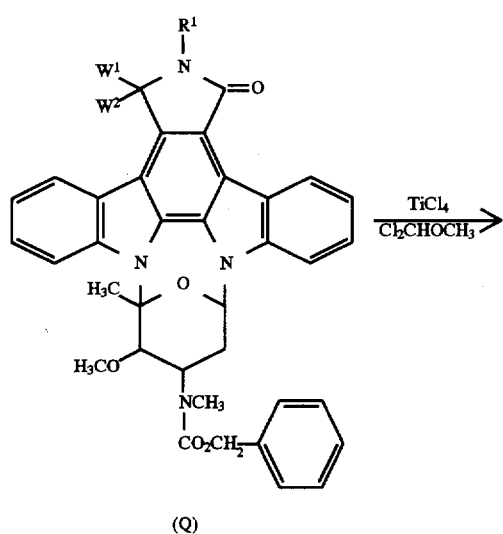

(Q)

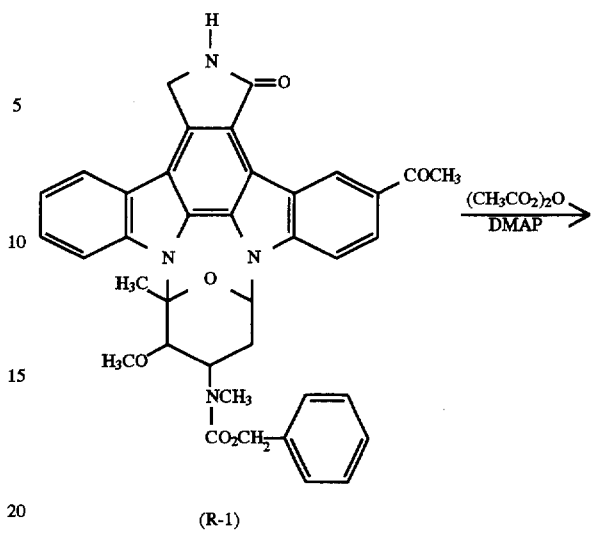

(R-1)

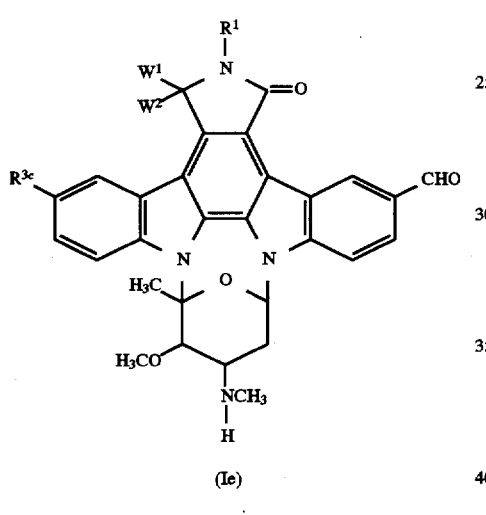

(Ie)

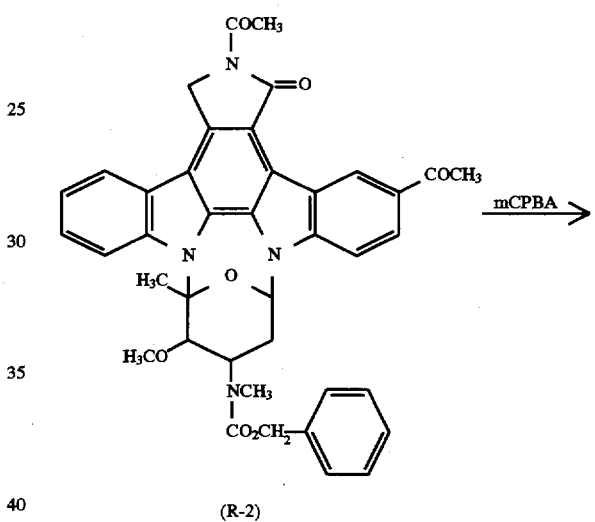

(R-2)

(In the formulae, $R^{3c}$ represents hydrogen or formyl; and $R^1$, $W^1$ and $W^2$ have the same meanings as defined above.)

Compound (Q) is allowed to react with dichloromethyl methyl ether in the presence of a Lewis acid such as titanium tetrachloride in an appropriate solvent such as dichloromethane to give Compound (Ie). Dichloromethyl methyl ether and Lewis acid are used in amounts of 1.5 to 3 equivalents based on Compound (Q). The reaction is carried out at −10° to 30° C. and is completed in 1 to 5 hours.

(6) Compound (If) [Compound I in which $R^2$ is lower alkoxy]

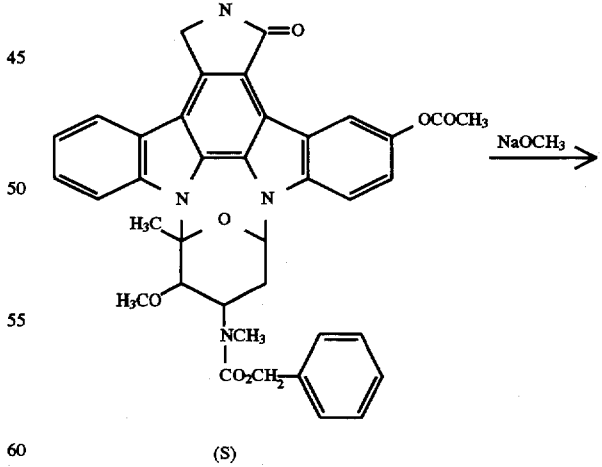

(S)

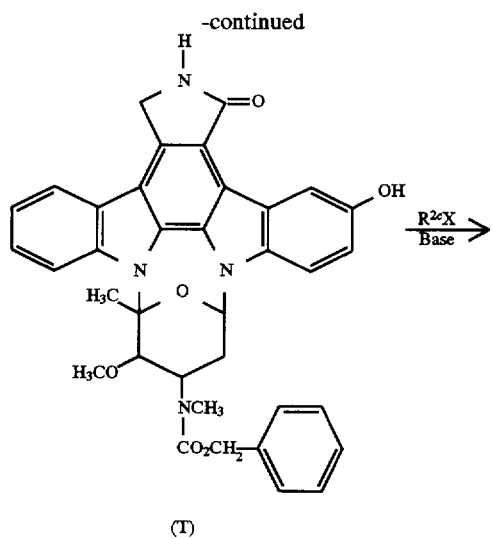

(T)

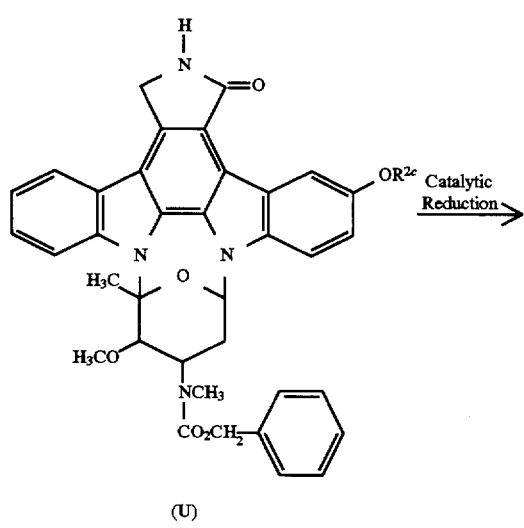

(U)

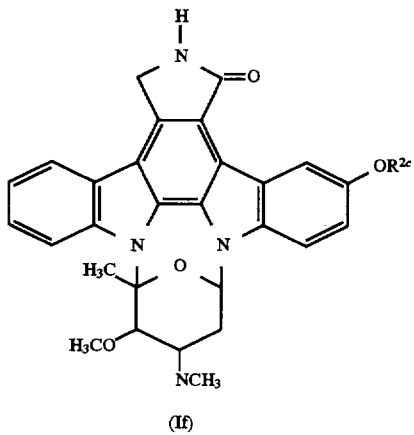

(If)

(In the formulae, $R^{2c}$ represents lower alkyl; and X has the same meaning as defined above.)

Compound (R-1) is allowed to react with acetic anhydride in the presence of a base such as 4-dimethylaminopyridine in an appropriate solvent such as THF to give Compound (R-2). 4-Dimethylaminopyridine and acetic anhydride are used in amounts of 1 to 8 equivalents and 5 to 20 equivalents, respectively, based on Compound (R-1). The reaction is carried out at 20° to 90° C. and is completed in 5 to 15 hours.

Compound (R-2) is allowed to react with an oxidizing agent such as m-chloroperbenzoic acid in the presence of a base such as sodium bicarbonate in an appropriate solvent such as chloroform to give compound (S). Sodium bicarbonate and m-chloroperbenzoic acid are used in amounts of 3 to 8 equivalents based on Compound (R-2). The reaction is carried out at 0° to 50° C. and is completed in 5 hours to one day.

Compound (S) is treated with sodium methylate or the like in an appropriate solvent such as dichloromethane to give Compound (T). Sodium methylate is used in an amount of 1 to 5 equivalents, and the reaction is completed in 5 to 30 minutes.

Compound (T) is allowed to react with $R^{2c}X$ in the presence of a base such as sodium hydride in an appropriate solvent such as DMF to give Compound (U). Sodium hydride and $R^{2c}X$ are used in amounts of 0.8 to 1.2 equivalents and 1 to 5 equivalents, respectively, based on Compound (T). The reaction is carried out at −10° to 20° C. and is completed in 1 to 5 hours.

Catalytic reduction of Compound (U) in the same manner as in the case of Compound (Ia) gives Compound (If).

(7) Compound (Ig) [Compound I in which $R^4$ is methoxymethyl]

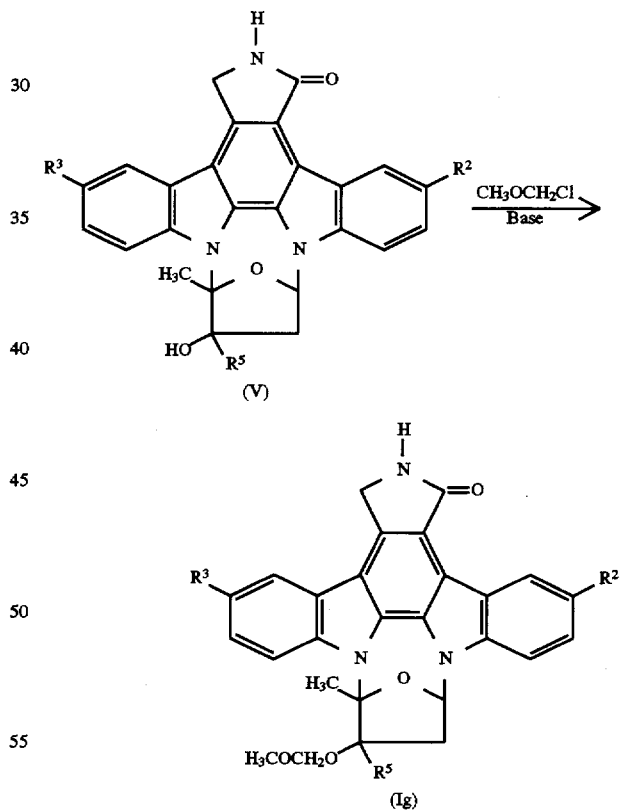

(In the formulae, $R^2$, $R^3$ and $R^5$ have the same meanings as defined above.)

Compound (V) is allowed to react with methoxymethyl chloride in the presence of a base such as sodium hydride in an appropriate solvent such as THF to give Compound (Ig). Sodium hydride and methoxymethyl chloride are used in amounts of 1 to 1.5 equivalents based on Compound (V). The reaction is carried out at 0° to 30° C. and is completed in 1 to 2 days.

(8) Compound (Ih) [Compound I in which $R^1$ is lower alkyl, $R^2$ is hydroxy, and $R^3$ is hydroxy or hydrogen]

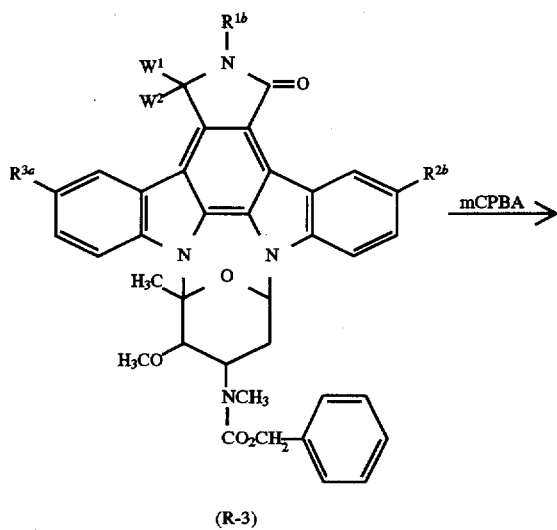

(R-3)

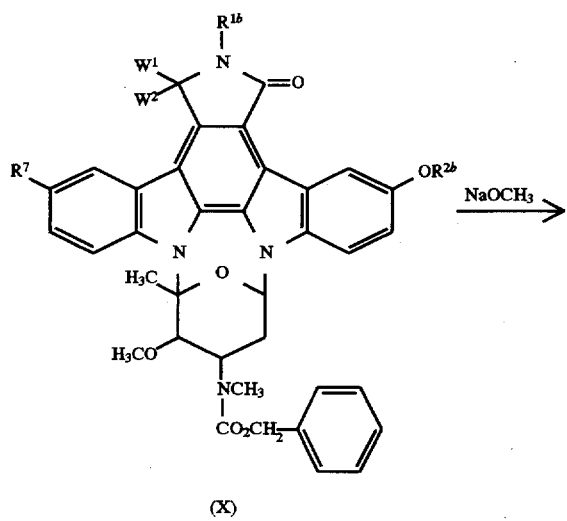

(X)

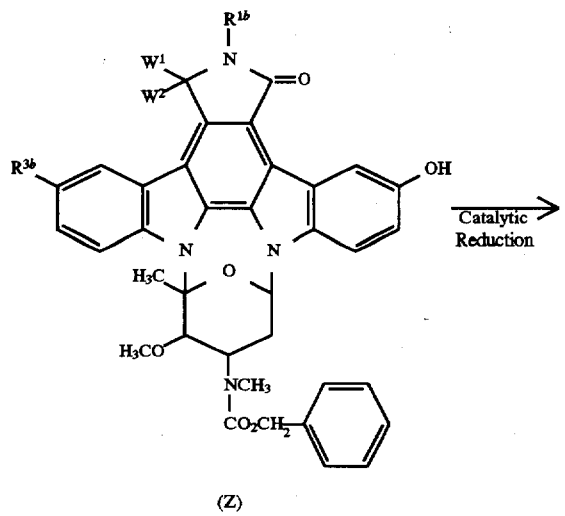

(Z)

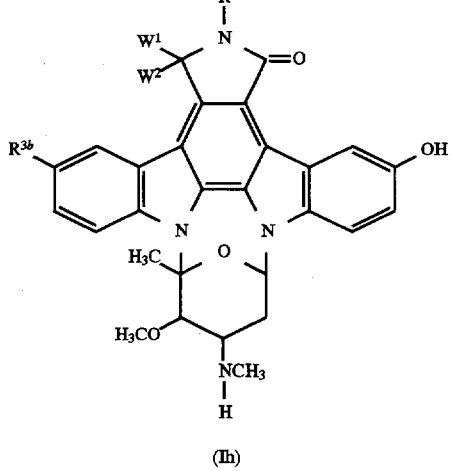

(Ih)

(In the formulae, $R^{1b}$ represents lower alkyl; $R^{3b}$ represents hydroxy or hydrogen; $R^7$ represents $OR^{3a}$ or hydrogen; and $W^1$, $W^2$, $R^{2b}$ and $R^{3a}$ have the same meanings as defined above.)

Treatment of Compound (R-3) following the same procedures as in the preparation of Compound (S) gives Compound (X). Compound (X) is treated in the same manner as in the preparation of Compound (T) to give Compound (Z). Treatment of Compound (Z) in the same manner as in the preparation of Compound (Ia) gives Compound (Ih).

Isolation and purification of the products in the above processes can be carried out using an appropriate combination of methods conventionally used in organic synthesis, for example, extraction, crystallization and various types of chromatography.

Data on the physical properties of known Compounds I-1 to 18, 28, 35–37 and 42–46 are given below.

Compound I-1 m.p. 245°–250° C. (dec.) $[\alpha]_D^{23}$ +132.0° (c=0.3, methanol)

Compound I-2 MS(m/z); 480 (M$^+$)

Compound I-3 MS(m/z); 496 (M+1)$^+$

Compound I-4 MS(m/z); 484 (M+1)$^+$

Compound I-5 m.p. 145°–147.5° C.

Compound I-6 MS(m/z); 526 (M+1)$^+$

Compound I-7 MS(m/z); 495 (M$^+$)

Compound I-8 MS(m/z); 551 (M$^+$)

Compound I-9 MS(m/z); 494 (M$^+$)

Compound I-10 MS(m/z); 581 (M$^+$)

Compound I-11 MS(m/z); 630 (M+1)$^+$

Compound I-13 MS(m/z); 571 (M$^+$)

Compound I-14 MS(m/z); 528 (M+1)$^+$

Compound I-15 MS(m/z); 509 (M$^+$)

Compound I-16 MS(m/z); 311 (M$^+$)

Compound I-17 MS(m/z); 466 (M)$^+$

Compound I-18 MS(m/z); 615 (M+1)$^+$

Compound I-28 MS(m/z); 509 (M+1)$^+$

Compound I-35 MS(m/z); 468 (M+1)$^+$

Compound I-36 MS(m/z); 481 (M)$^+$

Compound I-37 MS(m/z); 594 (M+1)$^+$

Compound I-42 MS(m/z); 495 (M)$^+$

Compound I-43 MS(m/z); 523 (M)$^+$

Compound I-44 MS(m/z); 523 (M)$^+$

Compound I-45 MS(m/z); 495 (M)⁺

Compound I-46 MS(m/z); 409 (M)⁺

The above compounds are described in the following publications: Japanese Published Unexamined Patent Application No. 220196/87 (EP-A-238011, U.S. Pat. No. 4,935, 415) (Compound I-1), WO 89-07105 (EP-A-383919) (Compounds I-2, 3, 9, 18 and 28), Japanese Published Unexamined Patent Application No. 168689/89 (EP-A-323171, U.S. Pat. No. 4,877,776) (Compounds I-4 and 14), Japanese Published Unexamined Patent Application No. 155284/87 (Compounds I-5, 15, 36, 42 and 45), Japanese Published Unexamined Patent Application No. 295588/88 (Compounds I-6, 7, 10, 11 and 37), J. Antibiotics, 38, 1437 (1985) (Compound I-8), Japanese Published Unexamined Patent Application No. 295589/88 (Compounds I-13, 43 and 44), J. Antibiotics, 39, 1066 (1986) (Compound I-16), Japanese Published Unexamined Patent Application No. 73501/78 (Compound I-17), Japanese Published Unexamined Patent Application No. 41489/85 (EP-A-137632, U.S. Pat. No. 4,555,402) (Compound I-35), and WO 88-07045 (Compound I-46).

The pharmacological effects of Compound I are shown below by test examples.

TEST EXAMPLE 1

Megakaryocyte colony formation-stimulating activity

An eight-weeks-old BALB/c mouse was killed. Its femurs and cervical vertebrae were taken out, and both end sections thereof were cut off. Bone marrow cells were collected from the pieces cut off from the femurs and cervical vertebrae using a syringe containing IMDM (430-2200EA prepared by Gibco Co.), and then blown into a test tube. The test tube was allowed to stand for 5 minutes, and the supernatant was collected with a pipet. To a reaction mixture comprising the bone marrow cells (50,000 cells), bovine serum albumin (2%: A4508 made by Sigma Co.), transferrin (600 μg/ml 652202 made by Boehringer Mannheim Co.), IL-3 (100 U/ml), cholesterol (16 μg/ml: 036-0641 made by Wako Co.) and agar (0.6%: 0142-02 made by Difco Laboratories) were separately added the test compounds at various concentrations, and 1 ml each of the mixtures was put into a 35-mm dish (Lux Co.), followed by incubation under the conditions of 37° C., 5% $CO_2$ and a humidity of 95% or more for 7 days. Separately, IL-3 alone was added to the bone marrow cells to prepare a control, whereas a positive control was prepared by adding 200 U/ml IL-6 to the above-mentioned reaction mixture. After the incubation was completed, the agar was dried over a filter paper (1001-055 made by Whatman Co.) and then fixed with 2.5% glutaraldehyde, followed by acetylcholinesterase staining (ACHE staining).

The ACHE staining was carried out by the method described below.

ACHE staining: To each sample was added a solution comprising 0.67 mg/ml acetylthiocholine iodide, 2.94 mg/ml sodium citrate, 7.5 mg/ml copper (II) sulfate and 1.65 mg/ml potassium ferricyanide, and the mixture was allowed to stand at room temperature in the dark for 4–6 hours.

A group of 4 or more megakaryocytes which were stained reddish brown was regarded as a colony, and the number of colonies per dish was calculated using a microscope. The results are shown in Table 2 as relative values to the control.

(The table shows the relative values calculated on the basis of the control defined as 100.)

TABLE 2

| Compound No. | Concentration (nM) | Relative value |
|---|---|---|
| Control |  | 100 |
| I-1 | 1 | 127 |
| I-2 | 0.01 | 125 |
|  | 1 | 168 |
| I-3 | 0.01 | 98.8 |
|  | 1 | 127 |
| I-4 | 0.01 | 94.3 |
|  | 1 | 115 |
| I-5 | 0.01 | 112 |
|  | 1 | 104 |
|  | 100 | 103 |
| I-6 | 0.01 | 112 |
|  | 1 | 132 |
|  | 100 | 117 |
| I-7 | 0.01 | 93 |
|  | 1 | 101 |
|  | 100 | 108 |
| I-8 | 0.01 | 95.6 |
|  | 1 | 118 |
|  | 100 | 89.6 |
| I-9 | 0.1 | 135 |
|  | 1 | 117 |
|  | 10 | 92.2 |
| I-10 | 0.1 | 122 |
|  | 1 | 139 |
|  | 10 | 133 |
| I-11 | 0.1 | 88.4 |
|  | 1 | 95 |
|  | 10 | 116 |
| I-12 | 0.1 | 133 |
|  | 1 | 113 |
|  | 10 | 122 |
| I-13 | 0.1 | 100 |
|  | 1 | 113 |
|  | 10 | 125 |
| I-14 | 0.1 | 118 |
|  | 1 | 115 |
|  | 10 | 116 |
| I-15 | 0.1 | 120 |
|  | 1 | 121 |
|  | 10 | 132 |
| I-16 | 0.1 | 118 |
|  | 1 | 88.3 |
|  | 10 | 100 |
| I-17 | 1.0 (pM) | 119 |
|  | 10 (pM) | 107 |
| I-18 | 0.1 | 118 |
|  | 1.0 | 88 |
|  | 10 | 84 |
| I-19 | 0.1 | 118 |
|  | 1.0 | 94 |
|  | 10 | 156 |
| I-20 | 0.1 | 107 |
|  | 1.0 | 131 |
|  | 10 | 144 |
| I-21 | 0.1 | 95 |
|  | 1.0 | 105 |
|  | 10 | 97 |
| I-22 | 0.1 | 116 |
|  | 1.0 | 120 |
|  | 10 | 100 |
| I-23a | 0.1 | 114 |
| I-23b | 0.1 | 114 |
| I-24 | 0.1 | 88 |
|  | 1.0 | 87 |
|  | 10 | 109 |
| I-25 | 0.1 | 119 |
|  | 1.0 | 124 |
|  | 10 | 100 |
| I-26 | 0.1 | 108 |
|  | 1.0 | 121 |
|  | 10 | 111 |
| I-27 | 0.1 | 76 |
|  | 1.0 | 109 |
|  | 10 | 97 |
| I-28 | 0.1 | 89 |

TABLE 2-continued

| Compound No. | Concentration (nM) | Relative value |
|---|---|---|
| | 1.0 | 101 |
| | 10 | 95 |
| I-29 | 0.1 | 90 |
| | 1.0 | 113 |
| | 10 | 112 |
| I-30 | 0.1 | 111 |
| | 1.0 | 119 |
| | 10 | 117 |
| I-31 | 0.1 | 76 |
| | 1.0 | 94 |
| | 10 | 109 |
| I-32 | 0.1 | 76 |
| | 1.0 | 94 |
| | 10 | 109 |
| I-33 | 0.1 | 101 |
| | 1.0 | 114 |
| | 10 | 105 |
| I-35 | 1.0 (pM) | 130 |
| | 10 (pM) | 140 |
| I-36 | 0.1 | 130 |
| | 1.0 | 172 |
| | 10 | 173 |
| I-37 | 0.1 | 82 |
| | 1.0 | 124 |
| | 10 | 114 |
| I-38 | 0.1 | 112 |
| | 1.0 | 111 |
| | 10 | 136 |
| I-39 | 0.1 | 123 |
| | 1.0 | 109 |
| | 10 | 92 |
| I-40 | 0.1 | 109 |
| | 1.0 | 125 |
| | 10 | 114 |
| I-42 | 0.1 | 91 |
| | 1 | 107 |
| | 10 | 122 |
| I-43 | 0.1 | 81 |
| | 1 | 118 |
| | 10 | 87 |
| I-44 | 0.1 | 126 |
| | 1 | 70 |
| | 10 | 118 |
| I-45 | 0.1 | 103 |
| | 1 | 143 |
| | 10 | 100 |
| I-46 | 0.1 | 97 |
| | 1 | 131 |
| | 10 | 112 |
| I-49 | 0.1 | 122 |
| | 1 | 128 |
| I-50 | 1 | 118 |
| | 10 | 128 |
| IL-6 | 200 U/ml | 117 |

TEST EXAMPLE 2

Platelet production-stimulating activity in mice

BALB/c mice (male, 7-weeks-old) were divided into 2 groups. To one group (control group) was administered a solvent (1% lactic acid, 4% aqueous solution of glucose) alone. On the other hand, the test group (Compound I-1-administered group) received 0.2 ml of a solution of Compound I-1 in the above solvent at a dose of 7.5 mg/kg via the caudal vein once a day for 5 days (Day 1–Day 5). On the day before the administration (Day 0) and the seventh day after the start of administration (Day 7), the ninth day (Day 9), the 14th day (Day 14) and the 21st day (Day 21), 20 μl of blood was collected from the fundus oculi vein of the mice of each group, and the number of the platelets was counted with a microcell counter (Type CC-180A made by Toa Iryo Denshi Co.). The results are shown in Table 3.

TABLE 3

| | Number of platelets ($\times 10^4/mm^3$) | | | | |
|---|---|---|---|---|---|
| Mouse No. | Day 0 | Day 7 | Day 9 | Day 14 | Day 21 |
| Control group | | | | | |
| #1 | 141.0 | 141.0 | 135.1 | 94.1 | 102.9 |
| #2 | 113.0 | 139.6 | 107.6 | 104.5 | 106.7 |
| #3 | 109.6 | 125.5 | 116.9 | 117.7 | 131.5 |
| #4 | 104.8 | 133.8 | 109.9 | 112.3 | 123.2 |
| #5 | 85.9 | 127.1 | 102.8 | 117.0 | 107.0 |
| (Average) | 110.9 | 133.4 | 114.5 | 109.1 | 114.3 |
| (Standard deviation) | 19.8 | 7.0 | 12.6 | 9.9 | 12.4 |
| % Relative value | 100 | 120.3 | 103.2 | 98.4 | 103.1 |
| Compound I-1 (7.5 mg/kg/day × 5)-administered group | | | | | |
| #8 | 92.6 | 103.1 | 125.3 | 125.3 | 133.9 |
| #9 | 90.5 | 91.8 | 160.0 | 106.4 | 202.7 |
| #10 | 94.2 | 119.4 | 160.0 | 121.1 | 153.0 |
| #11 | 117.6 | 155.7 | 144.5 | 145.4 | 139.6 |
| #13 | 111.7 | 136.3 | 136.1 | 112.3 | 135.5 |
| #14 | 95.5 | 111.2 | 146.8 | 115.0 | 163.9 |
| (Average) | 100.4 | 119.6 | 145.5 | 120.9 | 154.8 |
| (Standard deviation) | 11.4 | 23.2 | 13.6 | 13.6 | 26.2 |
| % Relative value | 100 | 119.1 | 144.9 | 120.4 | 154.2 |

TEST EXAMPLE 3

Acute toxicity test

To 6-weeks-old male DDY mice (3 per group) was intraperitoneally administered 0.2 ml of a solution of a test compound in a phosphate-buffered physiological saline. The 50% survival doses ($LD_{50}$) were calculated from the survival rate after 24 hours. The $LD_{50}$ for Compounds I-1, 17, 25, 26, 30–33, 35, 40 and 52 was >1 mg/kg, while that for all the other compounds was >30 mg/kg.

Compound I and pharmaceutically acceptable salts thereof can be used directly or in the form of various pharmaceutical compositions for the intended administration purpose depending on their pharmacological activity. The pharmaceutical compositions according to the present invention can be prepared by uniformly mixing an effective amount of Compound I or a pharmaceutically acceptable salt thereof as an active ingredient with a pharmaceutically acceptable carrier. The carrier may vary in form over a wide range depending on the type of the preparation desired for the administration. These pharmaceutical compositions are desired to be in a unit dose form which is appropriate for oral or non-oral administration. The forms for non-oral administration include ointment and injection.

Tablets can be prepared using, in a conventional manner, excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinylpyrrolidone, hydroxypropyl cellulose and methyl cellulose, surface active agents such as sucrose fatty acid ester and sorbitol fatty acid ester, etc. Tablets each containing 50–200 mg of an active ingredient are appropriate.

For the preparation of granules, excipients such as lactose and sucrose, disintegrating agents such as starch, binders such as gelatin, etc. may be used in a conventional manner. For the preparation of powders, excipients such as lactose and mannitol, etc. may be used in a conventional manner. Capsules can be prepared using, in a conventional manner, gelatin, water, sucrose, gum arabic, sorbitol, glycerine, crystalline cellulose, magnesium stearate, talc, etc. Capsules each containing 50–200 mg of an active ingredient are appropriate. For the preparation of syrups, saccharides such as sucrose, water, ethanol, and so on may be used in a conventional manner.

For the preparation of ointments, ointment bases such as vaseline, liquid paraffin, lanolin and macrogol, emulsifying agents such as sodium lauryl lactate, benzalkonium chloride, sorbitan mono-fatty acid ester, sodium carboxymethyl cellulose and gum arabic, etc. may be used in a conventional manner.

Injectable preparations can be prepared using, in a conventional manner, solvents such as water, physiological saline, vegetable oil (e.g., olive oil and peanut oil), ethyl oleate and propylene glycol, solubilizing agents such as sodium benzoate, sodium salicylate and urethane, isotonizing agents such as sodium chloride and glucose, preservatives such as phenol, cresol, p-hydroxybenzoic ester and chlorobutanol, antioxidants such as ascorbic acid and sodium pyrosulfite, etc.

Compound I and pharmaceutically acceptable salts thereof may be administered orally or non-orally as an ointment or an injection. The effective dose and the administration schedule vary depending on the mode of administration, the age, body weight and symptoms of the patient, etc. However, it is generally appropriate to administer them at a daily dose of 22.5–100 mg/m$^2$ in 1 to 4 parts.

BEST MODE FOR CARRYING OUT THE INVENTION

EXAMPLE 1: INJECTIONS

Compound I-1 (2.0 g) was dissolved in 20 l of ethanol, and the solution was subjected to pressure filtration through Millipore Filter (pore size: 0.22μ) for sterilization. The resulting sterile filtrate was put into brown vials in 5.0 ml portions and then lyophilized in a conventional manner to obtain 0.5 mg/vial of lyophilized preparations.

EXAMPLE 2: TABLETS

Tablets were prepared in a conventional manner using 180 mg of Compound I-1, 90 mg of lactose, 40 mg of corn starch, 4 mg of polyvinyl alcohol, 28 mg of Avicel and 1 mg of magnesium stearate.

EXAMPLE 3: INJECTIONS

Compound I-22 (2.0 g) was dissolved in 20 l of ethanol, and the solution was subjected to pressure filtration through Millipore Filter (pore size: 0.22μ) for sterilization. The resulting sterile filtrate was put into brown vials in 5.0 ml portions and then lyophilized in a conventional manner to obtain 0.5 mg/vial of lyophilized preparations.

EXAMPLE 4: TABLETS

Tablets were prepared in a conventional manner using 180 mg of Compound I-22, 90 mg of lactose, 40 mg of corn starch, 4 mg of polyvinyl alcohol, 28 mg of Avicel and 1 mg of magnesium stearate.

EXAMPLE 5: INJECTIONS

Compound I-48 (2.0 g) was dissolved in 20 l of ethanol, and the solution was subjected to pressure filtration through Millipore Filter (pore size: 0.22μ) for sterilization. The resulting sterile filtrate was put into brown vials in 5.0 ml portions and then lyophilized in a conventional manner to obtain 0.5 mg/vial of lyophilized preparations.

EXAMPLE 6: TABLETS

Tablets were prepared in a conventional manner using 180 mg of Compound I-48, 90 mg of lactose, 40 mg of corn starch, 4 mg of polyvinyl alcohol, 28 mg of Avicel and 1 mg of magnesium stearate.

EXAMPLE 7: SYNTHESIS OF COMPOUND I-20

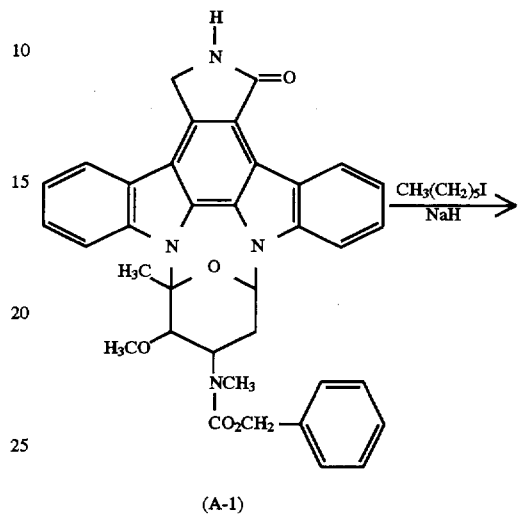

Compound (E) was obtained from 100 mg (0.16 mmol) of Compound (A-1) and 70 μl (0.48 mmol) of hexyl iodide by the same procedure as in the synthesis of Compound I-19 described in Reference Example 2 (yield: 60.6 mg, 55.4%).

$^1$H-NMR (DMSO-d$_6$) δ; 0.880 (t, 3H, J=7.1Hz), 1.302–1.385 (m, 6H), 1.780 (m, 2H), 2.683 (s, 3H), 2.740 (s, 3H), 3.696 (m, 1H), 5.059 (d, 1H, J=17.9Hz), 5.100 (d, 1H, J=17.9Hz), 7.007 (br. s, 1H), 7.274–8.112 (m, 7H), 9.304 (d, 1H, J=8.0Hz) Fab-MS(m/z); 685 (M+1)$^+$

Compound I-20 was obtained from 50 mg of Compound (E) and 50 mg of 10% Pd/C by the same procedure as in the synthesis of Compound I-19 described in Reference Example 2 (yield: 15 mg, 36%).

$^1$H-NMR (DMSO-d$_6$) δ; 0.833 (t, 3H, J=7.2Hz), 1.306–1.406 (m, 6H), 1.751–1.794 (m, 2H), 2.102 (m, 1H), 2.299 (s, 3H), 3.693 (m, 2H), 4.034 (m, 1H), 4.537 (s, 1H), 5.088 (s, 2H), 6.945 (dd, 1H, J=3.3, 9.5Hz), 7.305–8.149 (m, 7H), 9.337 (d, 1H, J=7.97Hz) Fab-MS (m/z); 551 (M+1)$^+$

EXAMPLE 8: SYNTHESIS OF COMPOUND I-21

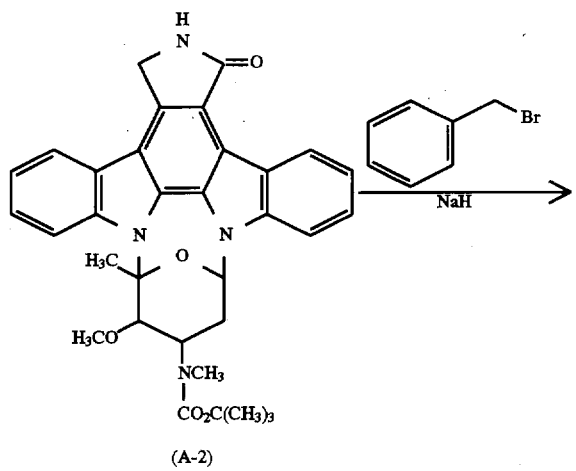

(A-2)

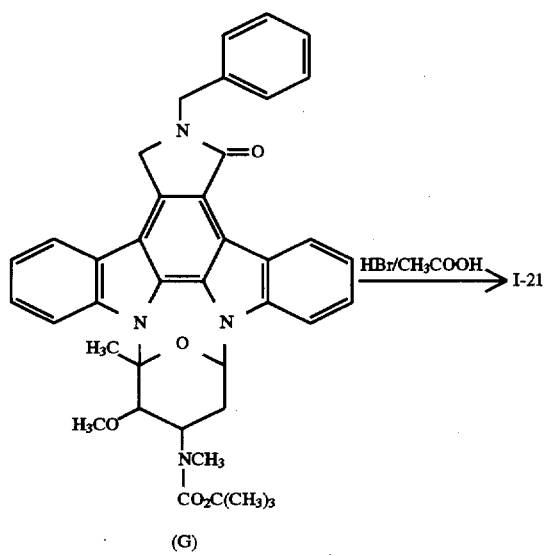

(G)

Compound (G) was obtained from 113.2 mg (0.2 mmol) of Compound (A-2) and 47.5 µl (0.4 mmol) of benzyl bromide by the same procedure as in the synthesis of Compound I-19 described in Reference Example 2 (yield: 40 mg, 31%).

$^1$H-NMR (DMSO-d$_6$) δ; 2.176 (dt, 1H, J=6.6, 13.0Hz), 2.343 (s, 3H), 2.644 (s, 3H), 2.777 (s, 3H), 4.271 (s, 1H), 4.904 (d, 1H, J=15.6Hz), 4.954 (d, 1H, J=15.6Hz), 5.028 (s, 2H), 7.030 (dd, 1H, J=6.9, 8.3Hz), 7.277–8.049 (m, 12H), 9.327 (d, 1H, J=7.8Hz) Fab-MS (m/z); 657 (M+1)$^+$

To a solution of 18 mg (0.027 mmol) of Compound (G) in 0.5 ml of chloroform was added 26.2 µl of 25% hydrobromic acid/acetic acid, followed by stirring at room temperature for one hour. The resulting precipitate was filtered off to give 14.4 mg (83.7%) of Compound I-21.

$^1$H-NMR (DMSO-d$_6$) δ; 2.082 (m, 1H), 2.271 (s, 3H), 2.708 (t, 3H, J=5.1Hz), 4.049 (m, 1H), 4.425. (d, 1H, J=1.0Hz), 4.893 (d, 1H, J=15.2Hz), 4.943 (d, 1H, J=15.2Hz), 5.013 (d, 1H, J=18.1Hz), 5.061 (d, 1H, J=18.1Hz), 6.957 (dd, 1H, J=3.0, 9.3Hz), 7.280–8.082 (m, 12H), 8.642 (br. s, 1H), 8.813 (br. s, 1H), 9.355 (d, 1H, J=8.1Hz) Fab-MS (m/z); 557 (M+1)$^+$

EXAMPLE 9: SYNTHESIS OF COMPOUND I-24

To a solution of 135 mg (0.28 mmol) of Compound I-2 in 5 ml of tetrahydrofuran (THF) were added 81.7 mg (1.41 mmol) of propionaldehyde and 28.3 mg (0.45 mmol) of sodium cyanoborohydride. The mixture was adjusted to pH 5–6 with 3N hydrochloric acid, and then stirred for 3.5 hours. After being adjusted to pH 1–2 with 3N hydrochloric acid, the mixture was made basic with 3N sodium hydroxide, followed by extraction with chloroform. The extract was washed with water and dried over sodium sulfate, and the chloroform was evaporated under reduced pressure to give a crude product. The product was purified by silica gel column chromatography (methanol/chloroform=1/50) to give 73.8 mg (yield 50%) of Compound I-24.

$^1$H-NMR (400 MHz, DMSO-d$_6$) δ; 9.324 (d, 1H, J=8.0Hz), 8.038 (m, 2H), 7.576 (d, 1H, J=8.3Hz), 7.469 (m, 2H), 7.321 (m, 2H), 6.835 (dd, 1H, J=3.1, 11.7Hz), 5.060 (s, 2H), 4.205 (s, 1H), 3.279 (s, 3H), 2.622 (s, 3H), 2.399 (s, 3H), 1.973 (s, 3H), 1.088 (m, 2H), 0.578 (t, 3H, J=7.3Hz) Fab-MS (m/z); 523 (M+1)$^+$

EXAMPLE 10: SYNTHESIS OF COMPOUND I-29

To a solution of 513 mg (1.1 mmol) of staurosporine (Compound I-17) in 30 ml of chloroform was added 66 µl of bromine at −23° C. The mixture was stirred for 4 hours, followed by addition of 20 ml of ether. The resulting precipitate was filtered off and then purified by HPLC (28% ammonium hydroxide/H$_2$O/methanol=1/15/85) to give 273 mg (43%) of Compound I-29.

$^1$H-NMR (DMSO-d$_6$) δ; 1.422 (s, 3H), 2.307 (s, 3H), 4.066 (d, 1H, J=3.5Hz), 4.959 (s, 2H), 6.710 (dd, 1H, J=2.2, 4.8Hz), 7.271–7.998 (m, 6H), 8.561 (s, 1H), 9.454 (d, 1H, J=1.9Hz) Fab-MS (m/z); 546 (M+1)$^+$

EXAMPLE 11: SYNTHESIS OF COMPOUND I-30

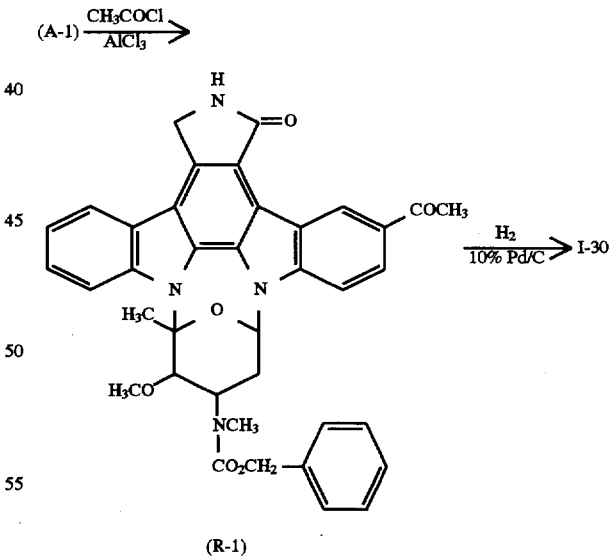

(R-1)

A solution of 333 mg (2.5 mmol) of aluminum chloride in 50 ml of dried dichloromethane was cooled to 0° C., and 88.9 µl (1.25 mmol) of acetyl chloride was added thereto, followed by stirring for 30 minutes. To the solution was added 500 mg (0.83 mmol) of Compound (A-1) dissolved in 25 ml of dichloromethane, and the mixture was stirred at 0° C. for 5 hours. After the completion of reaction, a saturated aqueous solution of sodium bicarbonate was added to the mixture, followed by extraction with chloroform. The extract was dried over sodium sulfate, and the solvent was evaporated. The residue was purified by silica gel column chromatography (2% methanol/chloroform) to give 333.3 mg (yield 62%) of Compound (R-1).

$^1$H-NMR (400 MHz, DMSO-$d_6$) δ; 10.015 (s, 1H), 8.630 (s, 1H), 8.111-8.071 (m, 2H), 7.988 (br. s, 1H), 7.725 (d, 1H, J=8.6Hz), 7.541-7.362 (m, 7H), 7.076 (s, 1H), 5.201 (s, 2H), 5.028 (s, 2H), 4.683 (br. s, 1H), 4.295 (br. s, 1H), 2.748 (s, 3H), 2.693 (s, 3H) Fab-MS (m/z); 643 (M+1)$^+$

Compound (R-1) (39.6 mg, 0.062 mmol) was subjected to the same reaction as in the preparation of Compound I-31 to give 16.3 mg (yield 52%) of Compound I-30.

$^1$-NMR (400 MHz, DMSO-$d_6$) δ; 10.015 (s, 1H), 8.531 (s, 1H), 8.087 (dd, 1H, J=1.8, 8.7Hz), 7.981 (t, 2H, J=7.1Hz), 7.700 (d, 1H, J=8.8Hz), 7.451-7.408 (m, 1H), 7.294 (t, 1H, J=7.4Hz), 6.774 (br. s, 1H), 4.978 (s, 2H), 4.648 (d, 1H, J=7.1Hz), 4.090 (d, 1H, J=3.4Hz), 3.384 (s, 3H), 2.757 (s, 3H), 2.326 (s, 3H), 1.417 (s, 3H) Fab-MS (m/z); 509 (M+1)$^+$

EXAMPLE 12: SYNTHESIS OF COMPOUND I-31

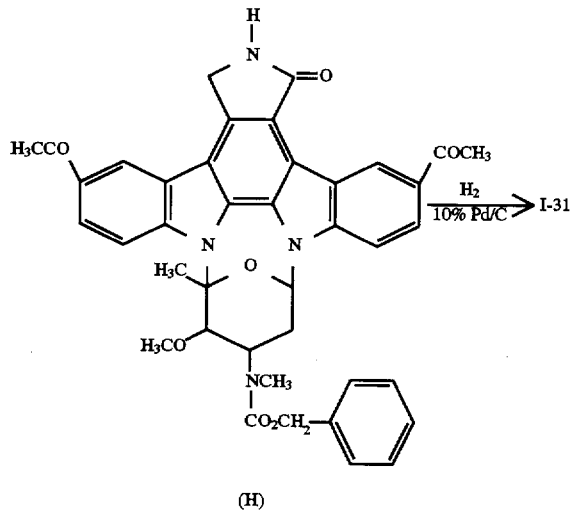

(H)

A solution of 1.11 g (8.33 mmol) of aluminum chloride in 30 ml of dried dichloromethane was cooled to 0° C., and 0.59 ml (8.33 mmol) of acetyl chloride was added thereto, followed by stirring for 30 minutes. To the solution was added 1.00 g (1.67 mmol) of Compound (A-1) dissolved in 15 ml of dichloromethane, followed by stirring at 0° C. for one hour. After a saturated aqueous solution of sodium bicarbonate was added, the reaction mixture was extracted with chloroform. The extract was washed with water and an aqueous solution of sodium chloride, and then dried over sodium sulfate. After the solvent was evaporated, the residue was purified by silica gel column chromatography (methanol/chloroform=1/50) to give 546.8 mg (yield 48%) of Compound (H).

$^1$H-NMR (400 MHz, DMSO-$d_6$) δ; 10.016 (s, 1H), 8.715 (s, 1H), 8.603 (s, 1H), 8.291 (s, 1H), 8.125-8.099 (m, 3H), 7.742 (d, 1H, J=8.8Hz), 7.408 (br. s, 5H), 7.094 (t, 1H, J=7.5Hz), 5.206 (s, 2H), 5.130 (s, 2H), 4.666 (br. s, 1H), 4.332 (br. s, 1H), 2.693 (s, 3H) Fab-MS (m/z); 685 (M+1)$^+$

To a solution of 50 mg (0.073 mmol) of Compound (H) in 3 ml of DMF was added 25 mg of 10% Pd/C, followed by stirring in an atmosphere of H$_2$ at room temperature for 5 hours. After the completion of reaction, the mixture was filtered through celite, and the solvent was evaporated to give a crude product. The product was purified by silica gel column chromatography (methanol/chloroform=1/9) to give 13.6 mg (yield 34%) of Compound I-31.

$^1$H-NMR (400 MHz, DMSO-$d_6$) δ; 10.024 (s, 1H), 8.626 (s, 1H), 8.520 (s, 1H), 8.289 (s, 1H), 8.111-8.015 (m, 3H), 7.729 (d, 1H, J=8.7Hz), 6.803 (d, 1H, J=4.4Hz), 5.084 (s, 2H), 4.116 (d, 1H, J=3.4Hz), 3.420 (s, 3H), 2.733 (s, 3H), 2.699 (s, 3H), 2.341 (s, 3H), 1.350 (br. s, 3H) Fab-MS (m/z); 551 (M+1)$^+$

EXAMPLE 13: SYNTHESIS OF COMPOUND I-32

To a solution of 50 mg (0.081 mmol) of Compound (A-1) in 4 ml of dried dichloromethane were added 149 µl (0.16 mmol) of titanium tetrachloride and 38 µl (0.16 mmol) of α,α-dichloromethyl methyl ether under cooling at 0° C., followed by stirring at 0° C. for 2.5 hours. After the completion of reaction, the mixture was diluted with 50 ml of chloroform, washed with a saturated aqueous solution of sodium bicarbonate and water, and then dried over sodium sulfate. The solvent was evaporated and the residue was purified by silica gel column chromatography (methanol/chloroform=1/20) to give 22.2 mg (yield 51%) of Compound I-32.

$^1$H-NMR (500 MHz, DMSO-$d_6$) δ; 10.099 (s, 1H), 9.821 (s, 1H), 9.227 (s, 1H), 8.698 (s, 1H), 8.592 (s, 1H), 7.994 (m, 3H), 7.800 (d, 1H, J=8.6Hz), 6.811 (br. s, 1H), 4.986 (s, 2H), 4.100 (br. s, 1H), 3.382 (s, 3H), 2.328 (s, 3H), 1.417 (br. s, 3H) Fab-MS (m/z); 523 (M+1)$^+$

EXAMPLE 14: SYNTHESIS OF COMPOUND I-33

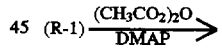

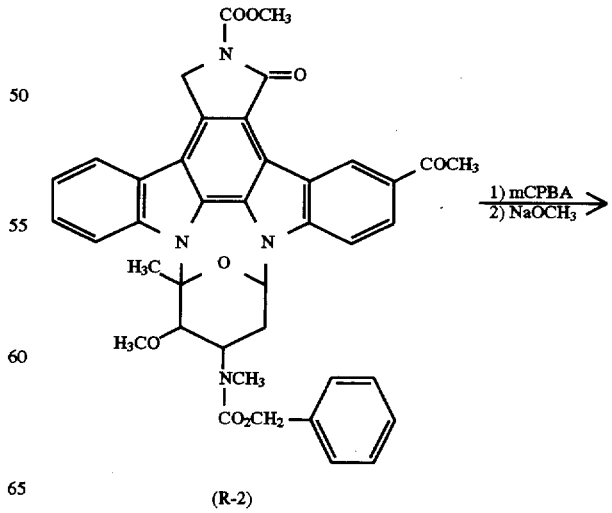

(R-2)

-continued

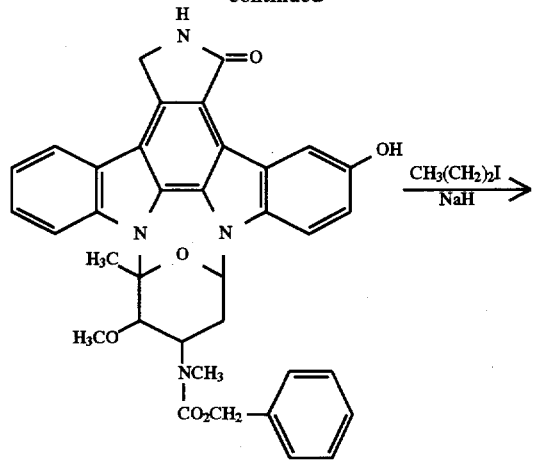

(T)

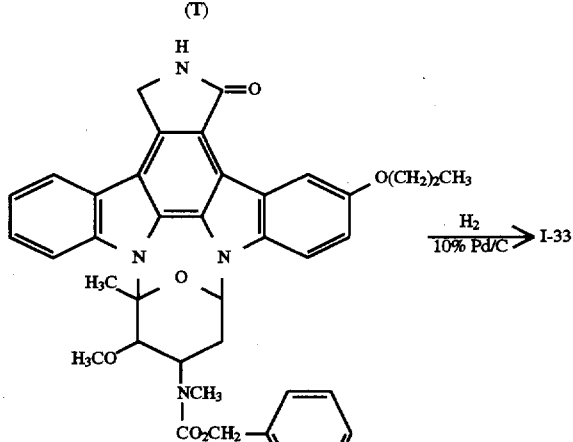

(M)

To a solution of 219.3 mg (0.34 mmol) of Compound (R-1) in 10 ml of tetrahydrofuran were added 0.32 ml (3.42 mmol) of acetic anhydride and 208.7 mg (1.71 mmol) of 4-dimethylaminopyridine. The mixture was subjected to reaction at 60° C. for 9 hours, followed by addition of 10 ml of methanol. After the reaction mixture was concentrated to a half of its original volume, an aqueous solution of sodium chloride was added thereto, followed by extraction with chloroform. The extract was dried over sodium sulfate, and the solvent was evaporated. The residue was purified by silica gel column chromatography (methanol/chloroform=1/100) to give 226.8 mg (yield 97%) of Compound (R-2).

$^1$H-NMR (400 MHz, DMSO-$d_6$) δ; 9.808 (s, 1H), 8.088 (dd, 1H, J=1.7, 8.8Hz), 8.060 (d, 1H, J=7.6Hz), 7.716 (d, 1H, J=8.5Hz), 7.562-7.395 (m, 8H), 7.049 (s, 1H), 5.351 (s, 2H), 5.198 (s, 1H), 4.666 (br. s, 1H), 4.280 (br. s, 1H), 3.264 (s, 3H), 2.733 (s, 3H), 2.650 (s, 3H) Fab-MS (m/z); 685 (M+1)$^+$

To a solution of 170 mg (0.25 mmol) of Compound (R-2) in 10 ml of chloroform were added 105 mg (1.25 mmol) of sodium bicarbonate and 214 mg (1.25 mmol) of m-chloroperbenzoic acid, and the mixture was subjected to reaction at room temperature for 8 hours. After the completion of reaction, the mixture was washed with a saturated aqueous solution of sodium sulfite, a saturated aqueous solution of sodium bicarbonate and water, and then dried over sodium sulfate. The solvent was evaporated, and the residue was dissolved in 10 ml of dichloromethane. The resulting solution was cooled to 0° C., and 246 μl (1.25 mmol) of a 28% solution of sodium methylate in methanol was added, followed by stirring for 10 minutes. After the completion of reaction, 2N diluted hydrochloric acid was added to the mixture for neutralization, followed by extraction with chloroform. The extract was washed with water, and then dried over sodium sulfate. The solvent was evaporated, and the residue was purified by silica gel column chromatography (5% methanol/chloroform) to give 90.9 mg (yield 59%) of Compound (T).

$^1$H-NMR (500 MHz, DMSO-$d_6$) δ; 9.032 (br. s, 1H), 8.712 (s, 1H), 8.495 (s, 1H), 8.032 (d, 1H, J=7.4Hz), 7.579-7.304 (m, 8H), 6.959 (dd, 1H, J=2.5, 8.6Hz), 6.893 (br. s, 1H), 5.190 (s, 2H), 4.957 (s, 2H), 4.675 (br. s, 1H), 4.260 (br. s, 1H), 2.746 (s, 3H), 2.686 (br. s, 3H) Fab-MS (m/z); 616 (M+1)$^+$

To a solution of 50 mg (0.081 mmol) of Compound (T) in 2 ml of dried DMF was added 3.2 mg (0.081 mmol) of 60% sodium hydride in oil under cooling at 0° C., followed by stirring for 30 minutes. Then, 41 μl (5 equivalents) of 1-iodopropane was added to the solution, and the mixture was stirred at 0° C. for 3 hours. After the completion of reaction, the mixture was diluted with 50 ml of chloroform, washed with a saturated aqueous solution of ammonium chloride and an aqueous solution of sodium chloride, and then dried over sodium sulfate. The solvent was evaporated, and the residue was purified by silica gel column chromatography (methanol/chloroform=1/200) to give 20.5 mg (yield 38%) of Compound (M).

$^1$H-NMR (400 MHz, DMSO-$d_6$) δ; 8.909 (s, 1H), 8.510 (s, 1H), 8.050 (d, 1H, J=8.1Hz), 7.527-7.331 (m, 8H), 7.132 (dd, 1H, J=2.7, 8.8Hz), 6.942 (br. s, 1H), 5.193 (s, 2H), 4.977 (s, 2H), 4.678 (br. s, 1H), 4.262 (br. s, 1H), 4.042 (t, 2H, J=6.6Hz), 2.741 (s, 3H), 2.675 (s, 3H), 1.850-1.798 (m, 2H), 1.055 (t, 3H, J=7.4Hz) Fab-MS (m/z); 658 (M+1)$^+$

To a solution of 19.6 mg (0.030 mmol) of Compound (M) in 2 ml of DMF was added 10 mg of 10% Pd/C, followed by stirring in an atmosphere of $H_2$ at room temperature for 2 hours. After the completion of reaction, the mixture was filtered through celite, and the solvent was evaporated to give a crude product. The product was purified by preparative TLC (10% methanol/chloroform) to give 11.3 mg (yield 72%) of Compound I-33.

$^1$H-NMR (500 MHz, DMSO-$d_6$) δ; 8.902 (s, 1H), 8.426 (br. s, 1H), 7.986-7.944 (m, 2H), 7.490 (d, 2H, J=8.8Hz), 7.409 (t, 1H, J=7.9Hz), 7.279 (t, 1H, J=7.4Hz), 7.111 (dd, 1H, J=2.6, 8.8Hz), 6.672 (br. s, 1H), 4.932 (s, 2H), 4.087 (br. s, 1H), 4.042 (t, 2H, J=6.8Hz), 2.317 (s, 3H), 1.849-1.807 (m, 2H), 1.063 (t, 3H, J=7.4Hz) Fab-MS (m/z); 525 (M+1)$^+$

EXAMPLE 15: SYNTHESIS OF COMPOUND I-39

To a solution of 103 mg (0.224 mmol) of K-252a (Compound I-35) in 11 ml of THF was added 14 mg of 60% sodium hydride at room temperature, followed by stirring for 10 minutes. Then, 20 μl of methoxymethyl chloride was added, and the mixture was stirred overnight. The reaction mixture was diluted with chloroform, washed with water and an aqueous solution of sodium chloride, and then dried over sodium sulfate. After the solvent was evaporated, the residue was purified by silica gel column chromatography (chloroform) to give 34.8 mg (30.9%) of Compound I-39.

$^1$H-NMR (CDCl$_3$) δ; 2.258 (s, 3H), 2.467 (dd, 1H, J=5.4, 13.9Hz), 2.625 (s, 3H), 3.378 (dd, 1H, J=7.3, 13.9Hz), 4.025

(s, 3H), 4.480 (d, 1H, J=7.4Hz), 4.560 (d, 1H, J=7.4Hz), 5.075 (s, 2H), 6.537 (br. s, 1H), 7.001 (dd, 1H, J=5.3, 7.2Hz), 7.346–7.953 (m, 7H), 9.334 (d, 1H, J=7.9Hz) SIMS (m/z); 512 (M+1)$^+$
EXAMPLE 16: SYNTHESIS OF COMPOUND I-51
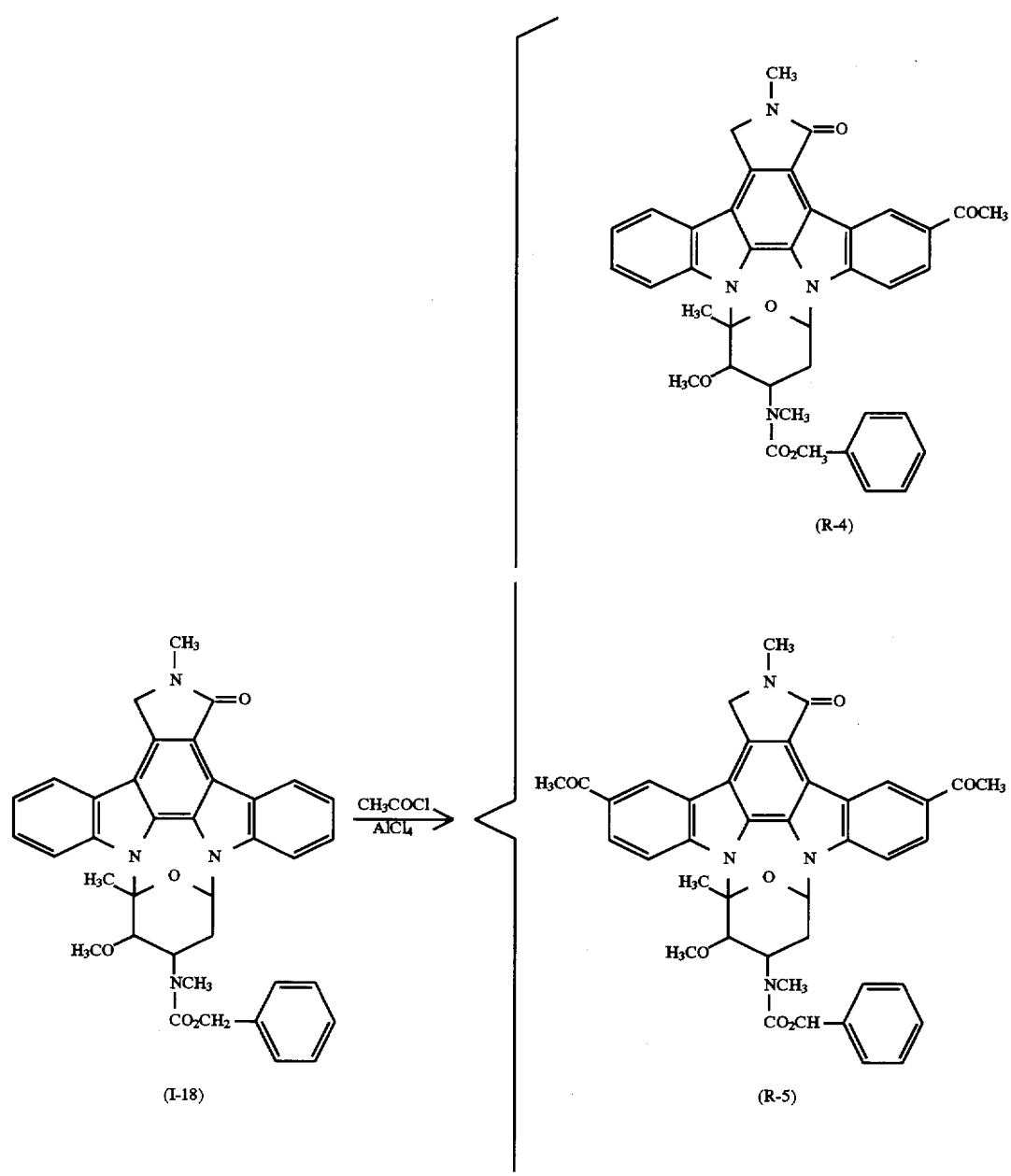

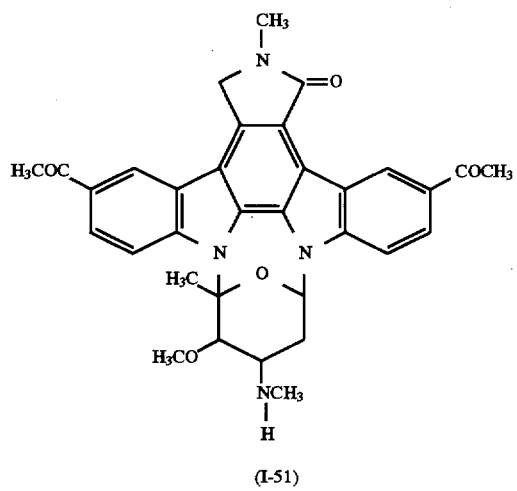

(I-51)

A solution of 1.05 g (7.89 mmol) of aluminum chloride in 100 ml of dried dichloromethane was cooled to 0° C., and 0.56 ml (7.89 mmol) of acetyl chloride was added thereto, followed by stirring for 30 minutes. To the solution was added 0.97 g (1.58 mmol) of Compound I-18 dissolved in 25 ml of dichloromethane, followed by stirring at 0° C. for 3 hours. The mixture was made basic with a saturated aqueous solution of sodium bicarbonate, and extracted with chloroform. The extract was washed with water and an aqueous solution of sodium chloride, and then dried over sodium sulfate. After the solvent was evaporated, the residue was purified by silica gel column chromatography (methanol/chloroform=1/50) to give 0.21 g (yield 21%) of Compound (R-4), 0.40 g (yield 35%) of Compound (R-5), and 0.15 g (yield 17%) of Compound I-51.

Compound (R-4)

$^1$H-NMR (500 MHz, DMSO-$d_6$) δ; 10.041 (s, 1H), 8.085 (t, 2H, J=8.8Hz), 7.721 (d, 2H, J=9.3Hz), 7.543-7.312 (m, 8H), 5.197 (s, 2H), 5.116 (s, 2H), 4.693 (br. s, 1H), 4.288 (br. s, 1H), 2.744 (s, 3H), 2.698 (s, 3H) Fab-MS (m/z); 657 (M+1)$^+$

Compound (R-5)

$^1$H-NMR (500 MHz, DMSO-$d_6$) δ; 10.032 (s, 1H), 8.587 (s, 1H), 8.106-8.086 (m, 3H), 7.724 (d, 1H, J=8.6Hz), 7.402 (br. s, 5H), 7.077 (t, 1H, J=7.6Hz), 5.234 (s, 4H), 2.755 (s, 3H), 2.738 (s, 3H), 2.690 (s, 6H) Fab-MS (m/z); 699 (M+1)$^+$

Compound I-51

$^1$H-NMR (500 MHz, DMSO-$d_6$) δ; 10.044 (s, 1H), 8.514 (s, 1H), 8.103-8.030 (m, 3H), 7.729 (d, 1H, J=8.8Hz), 6.795 (d, 1H, J=5Hz), 5.161 (s, 2H), 4.113 (s, 1H), 3.412 (s, 3H), 2.732 (s, 3H), 2.701 (s, 3H), 2.340 (s, 3H) Fab-MS (m/z); 565 (M+1)$^+$

EXAMPLE 17: SYNTHESIS OF COMPOUND I-48

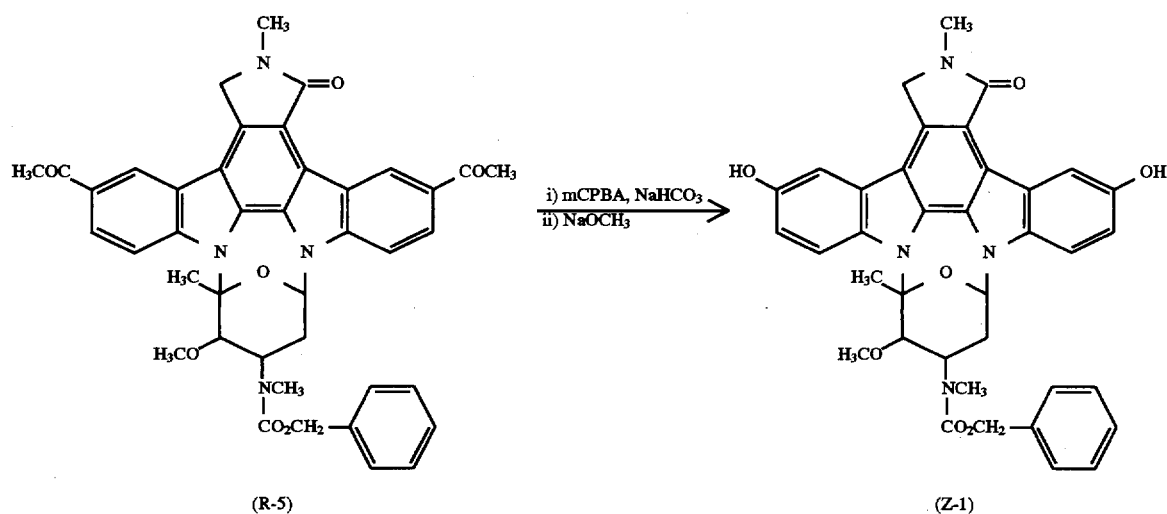

To a solution of 222.9 mg (0.32 mmol) of Compound (R-5) in 20 ml of chloroform were added 108.9 mg (1.30 mmol) of sodium bicarbonate and 419.3 mg (2.43 mmol) of m-chloroperbenzoic acid, and the mixture was subjected to reaction at room temperature for 8 hours. After the completion of reaction, the mixture was washed with a saturated aqueous solution of sodium sulfite, a saturated aqueous solution of sodium bicarbonate and water, and then dried over sodium sulfate. The solvent was evaporated, and the residue was dissolved in 20 ml of dichloromethane. The resulting solution was cooled to 0° C., and 237 μl (0.97 mmol) of a 28% solution of sodium methylate in methanol was added, followed by stirring for 10 minutes. After the completion of reaction, 2N hydrochloric acid was added to the mixture for neutralization, followed by extraction with chloroform. The extract was washed with water, and then dried over sodium sulfate. The solvent was evaporated, and the residue was purified by silica gel column chromatography (5% methanol/chloroform) to give 112.6 mg (yield 54%) of Compound (Z-1).

$^1$H-NMR (500 MHz, DMSO-$d_6$) δ; 9.208 (s, 1H), 9.007 (s, 1H), 8.716 (s, 1H), 7.718-7.646 (m, 2H), 7.571-7.300 (m, 6H), 6.973-6.937 (m, 2H), 6.855 (br. s, 1H), 5.181 (s, 2H), 4.977 (s, 2H), 4.635 (br. s, 1H), 4.137 (br. s, 1H), 2.733 (s, 3H), 2.635 (s, 3H) Fab-MS (m/z); 646 (M)$^+$ followed by stirring in an atmosphere of hydrogen at room temperature for 2 hours. The reaction mixture was filtered through celite, and the solvent was evaporated to give a crude product. The product was dissolved in a small quantity of methanol, followed by addition of 10 ml of 0.61N hydrochloric acid/ethyl acetate. The resulting precipitate was filtered off and dried to give 165 mg (yield 97%) of Compound I-48.

$^1$H-NMR (400 MHz, DMSO-$d_6$) δ; 8.750 (s, 1H), 7.857 (d, 1H, J=9Hz), 7.369-7.323 (m, 2H), 7.023-6.969 (m, 2H), 6.828 (dd, 1H, J=3, 9.3Hz), 4.991 (s, 2H), 4.388 (s, 1H), 3.978 (br. s, 1H), 2.666 (s, 3H), 2.426 (s, 3H), 2.291 (s, 3H) Fab-MS(m/z); 513 (M+1)$^+$

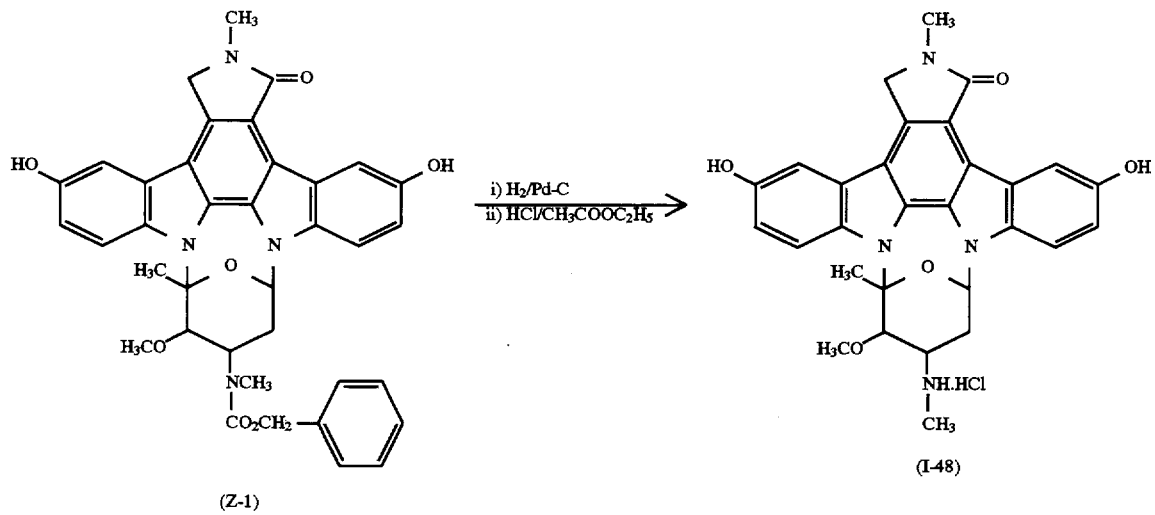

To a solution of 199.3 mg (0.31 mmol) of Compound (Z-1) in 10 ml of DMF was added 100 mg of 10% Pd/C,

EXAMPLE 18: SYNTHESIS OF COMPOUND I-47

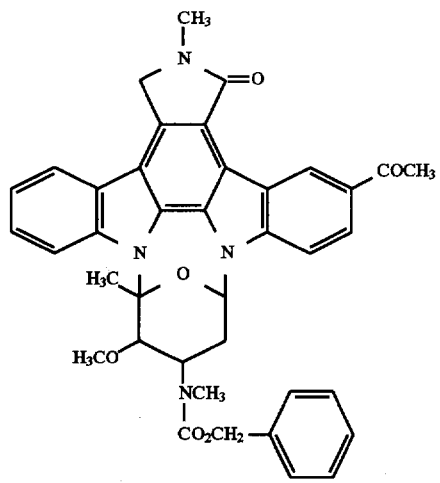
(R-4)

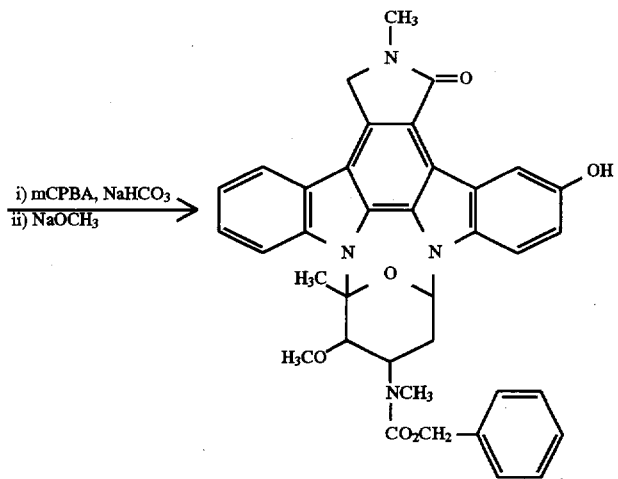
(Z-2)

Compound (R-4) (437 mg, 0.08 mmol) was subjected to the same reaction as in the preparation of Compound (Z-1) to give 292 mg (yield 69%) of Compound (Z-2).

$^1$H-NMR (500 MHz, DMSO-$d_6$) δ; 9.039 (s, 1H), 8.738 (s, 1H), 8.034 (d, 1H, J=7.2Hz), 7.588-7.306 (m, 8H), 6.981 (dd, 1H, J=2.5, 8.7Hz), 6.889 (br. s, 1H), 5.189 (s, 2H), 5.044 (s, 2H), 4.497 (br. s, 1H), 4.256 (br. s, 1H), 2.742 (s, 3H), 2.665 (s, 3H) Fab-MS (m/z); 630 (M)$^+$

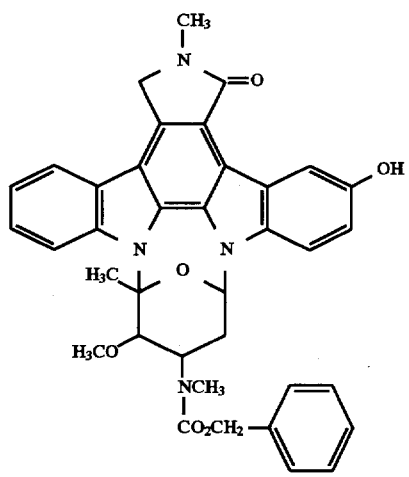
(Z-2)

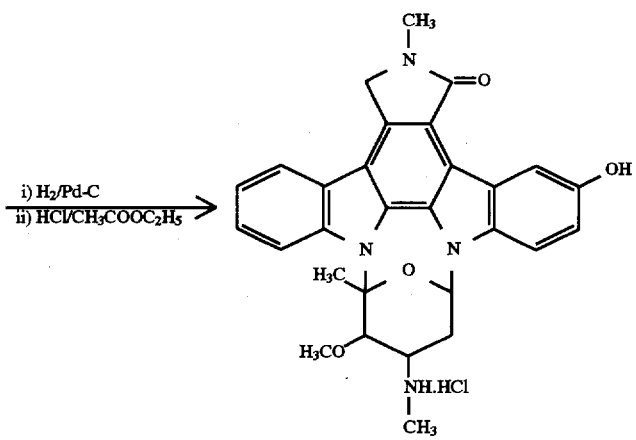
(I-47)

Compound (Z-2) (200 mg, 0.32 mmol) was subjected to the same reaction as in the preparation of Compound (I-48) to give 162 mg (yield 95%) of Compound (I-47).

$^1$H-NMR (400 MHz, DMSO-$d_6$) δ; 8.773 (s, 1H), 8.076-8.046 (m, 2H), 7.529 (t, 1H, J=8.6Hz), 7.414-7.344 (m, 2H), 7.018 (dd, 1H, J=2.5, 8.8Hz), 6.856 (dd, 1H, J=3.2, 9.3Hz), 5.057 (s, 2H), 4.476 (s, 1H), 4.006 (br. s, 1H), 2.680 (s, 3H), 2.292 (s, 3H) Fab-MS (m/z); 497 (M+1)$^+$

EXAMPLE 19: SYNTHESIS OF COMPOUND I-50

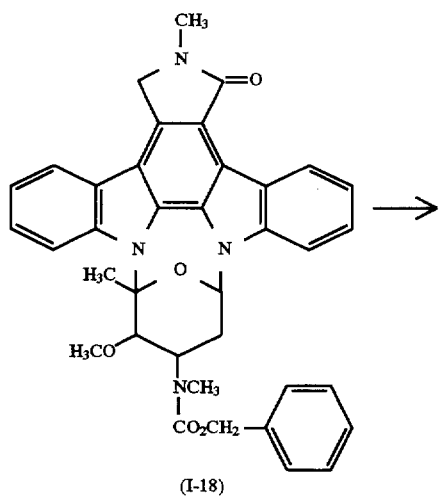
(I-18)

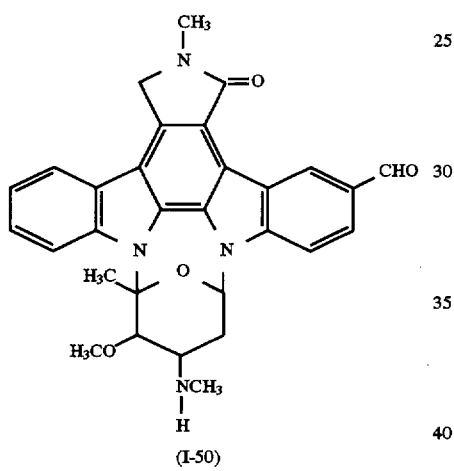
(I-50)

To a solution of 300 mg (0.49 mmol) of Compound (I-18) in 30 ml of dried dichloromethane were added 107 μl (0.98 mmol) of titanium tetrachloride and 133 μl (1.47 mmol) of α,α-dichloromethyl methyl ether under cooling at 0° C., followed by stirring at 0° C. for 2.5 hours. After the completion of reaction, the mixture was diluted with 100 ml of chloroform, washed with a saturated aqueous solution of sodium bicarbonate and water, and then dried over sodium sulfate. The solvent was evaporated, and the residue was purified by silica gel column chromatography (methanol/chloroform=3/100) to give 102.3 mg (yield 33%) of Compound I-50.

$^1$H-NMR (500 MHz, DMSO-$d_6$) δ; 10.102 (s, 1H), 9.848 (s, 1H), 8.014–7.980 (m, 3H), 7.793 (d, 1H, J=8.5Hz), 7.454 (t, 1H, J=7.5Hz), 7.317 (t, 1H, J=7.4Hz), 6.816 (br. s, 1H), 5.075 (s, 2H), 4.111 (br. s, 1H), 2.362 (s, 3H) Fab-MS (m/z); 509 (M+1)$^+$

EXAMPLE 20: SYNTHESIS OF COMPOUND I-49

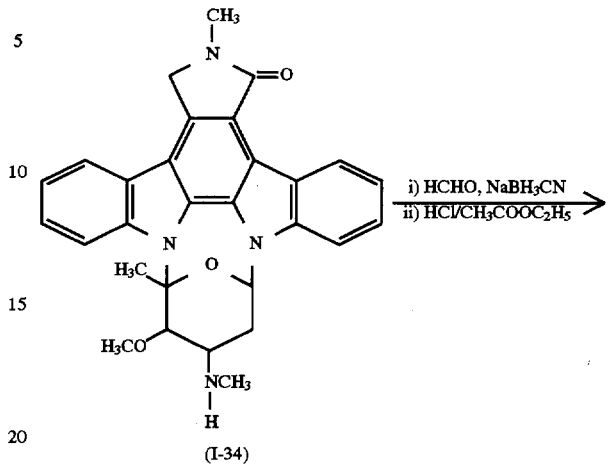
(I-34)

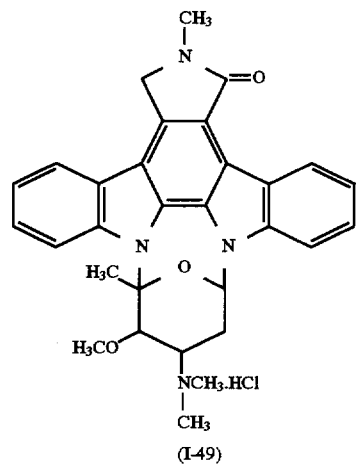
(I-49)

To a solution of 200 mg (0.42 mmol) of Compound (I-34) in 10 ml of THF were added 179 μl (2.08 mmol) of a 35% formaldehyde solution and 26.2 mg (0.42 mmol) of sodium cyanoborohydride, and the mixture was adjusted to pH 5–6 with 2N hydrochloric acid, followed by stirring for 2.5 hours. After the completion of reaction, the mixture was diluted with 100 ml of chloroform, washed with a saturated aqueous solution of sodium bicarbonate and an aqueous solution of sodium chloride and then dried over sodium sulfate. After the solvent was evaporated, the residue was purified by silica gel column chromatography (methanol/chloroform=1/20). Compound I-49 in the free form was dissolved in a small quantity of chloroform, and 10 ml of 0.61N hydrochloric acid/ethyl acetate was added to the solution. The resulting precipitate was filtered and dried to give 157.2 mg (71%) of Compound I-49.

$^1$H-NMR (400 MHz, CDCl$_3$) δ; 9.505 (d, 1H, J=7.3Hz), 7.943 (d, 1H, J=7Hz), 7.847 (d, 1H, J=9Hz), 7.516-7.240 (m, 6H), 6.649-6.621 (m, 1H), 4.984 (s, 2H), 3.973 (br. s, 1H), 3.004 (br. s, 1H), 2.734 (s, 3H), 2.657-2.626 (m, 2H), 2.415 (s, 3H), 1.967 (s, 6H) Fab-MS (m/z); 495 (M+1)$^+$

REFERENCE EXAMPLE 1: SYNTHESIS OF COMPOUND I-12

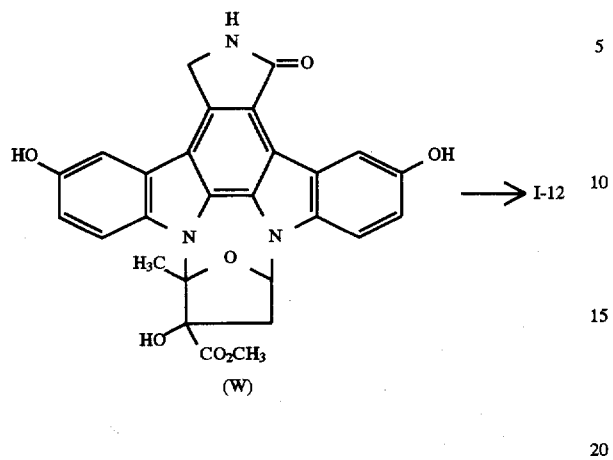

To a solution of 99 mg (0.2 mmol) of Compound (W) (Japanese Published Unexamined Patent Application No. 295588/88) in 2 ml of dimethylformamide was added 16 mg (0.4 mmol) of 60% sodium hydride under ice-cooling. The solution was stirred for 10 minutes, and 0.04 ml (0.4 mmol) of n-propyl iodide was added thereto, followed by stirring for one hour under ice-cooling. A saturated aqueous solution of ammonium chloride was added to the reaction mixture, followed by extraction with chloroform. The organic layer was washed with a saturated aqueous solution of sodium chloride and dried over anhydrous magnesium sulfate. After the solvent was evaporated, the residue was crystallized from tetrahydrofuran-chloroform to give 98 mg (yield 84%) of Compound I-12.

$^1$H-NMR (CDCl$_3$/DMSO-d$_6$ 10/1) δ; 2.09 (t, 6H, J=8Hz), 2.12 (s, 3H, CH$_3$), 4.96 (s, 2H), 6.17 (s, 1H, OH), 8.24 (s, 1H), 8.82 (s, 1H) MS (m/z); 583 (M)$^+$

REFERENCE EXAMPLE 2: SYNTHESIS OF COMPOUND I-19

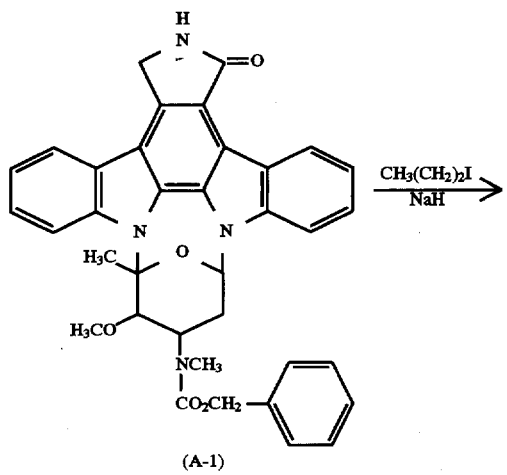

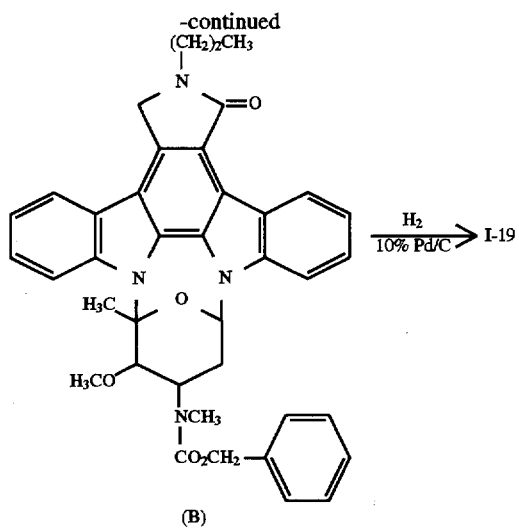

To a solution of 90 mg (0.15 mmol) of Compound (A-1) in 4.5 ml of DMF was added 9 mg (0.22 mmol) of 60% sodium hydride at −23° C. After 10 minutes, 45 μl of n-propyl iodide was added to the solution, followed by stirring for 2 hours. A 5% aqueous solution of citric acid was added, and the reaction mixture was diluted with chloroform, washed with water and an aqueous solution of sodium chloride, and then dried over sodium sulfate. After the solvent was evaporated, the residue was purified by silica gel column chromatography (acetone/toluene=1/9) to give 78.8 mg (82%) of Compound (B).

$^1$H-NMR (DMSO-d$_6$) δ; 0.975 (t, 3H, J=7.3Hz), 1.801 (m, 2H), 2.732 (s, 3H), 2.736 (s, 3H), 3.669 (m, 2H), 4.275 (br. s, 1H), 4.678 (br. s, 1H), 5.086 (s, 2H), 5.197 (s, 2H), 7.005 (br. s, 1H), 7.271–8.110 (m, 7H), 9.311 (d, 1H, J=7.8Hz) Fab-MS (m/z); 643 (M+1)$^+$

To a solution of 25 mg of Compound (B) in 1 ml of DMF was added 25 mg of 10% Pd/C, followed by stirring in an atmosphere of H$_2$ at 50° C. for 1.5 hours. After the reaction mixture was filtered through celite, the solvent was evaporated, and the residue was purified by preparative TLC (methanol/chloroform=3/97). Then, the product was dissolved in 1 ml of chloroform, and 1 ml of 0.06N hydrochloric acid/ethyl acetate was added to the solution. The resulting precipitate was filtered off to give 10.7 mg (51%) of Compound I-19.

$^1$H-NMR (DMSO-d$_6$) δ; 0.986 (t, 3H, J=7.28Hz), 1.807 (m, 2H), 2.102 (m, 1H), 2.296 (s, 3H), 2.686 (s, 3H), 3.668 (t, 2H, J=7.2Hz), 4.033 (m, 1H), 4.516 (s, 1H), 5.097 (s, 2H), 6.950 (dd, 1H, J=3.1, 9.5Hz), 7.305–8.147 (m, 7H), 8.978 (br. s, 1H), 9.185 (br. s, 1H), 9.339 (d, 1H, J=8.1Hz) Fab-MS (m/z); 509 (M+1)$^+$

REFERENCE EXAMPLE 3: SYNTHESIS OF COMPOUND I-22

To a solution of 1.6 g of Compound I-2 in 450 ml of THF and 200 ml of ethanol was added 70 ml of an aqueous solution of 444 mg of aspartic acid. After the organic solvent was evaporated, the residue was lyophilized to give 1.91 g of Compound I-22.

$^1$H-NMR (DMSO-d$_6$) δ; 1.476 (s, 3H), 2.316 (s, 3H), 2.422 (dd, 1H, J=3.2, 15.8Hz), 2.726 (dd, 1H, J=11.3, 15.8Hz), 3.752 (dd, 1H, J=3.2, 11.3Hz), 4.081 (d, 1H, J=3.4Hz), 5.031 (s, 2H), 6.723 (m, 1H), 7.246–7.999 (m, 7H), 9.291 (d, 1H, J=7.3Hz)

REFERENCE EXAMPLE 4: SYNTHESIS OF COMPOUNDS I-23a AND I-23b

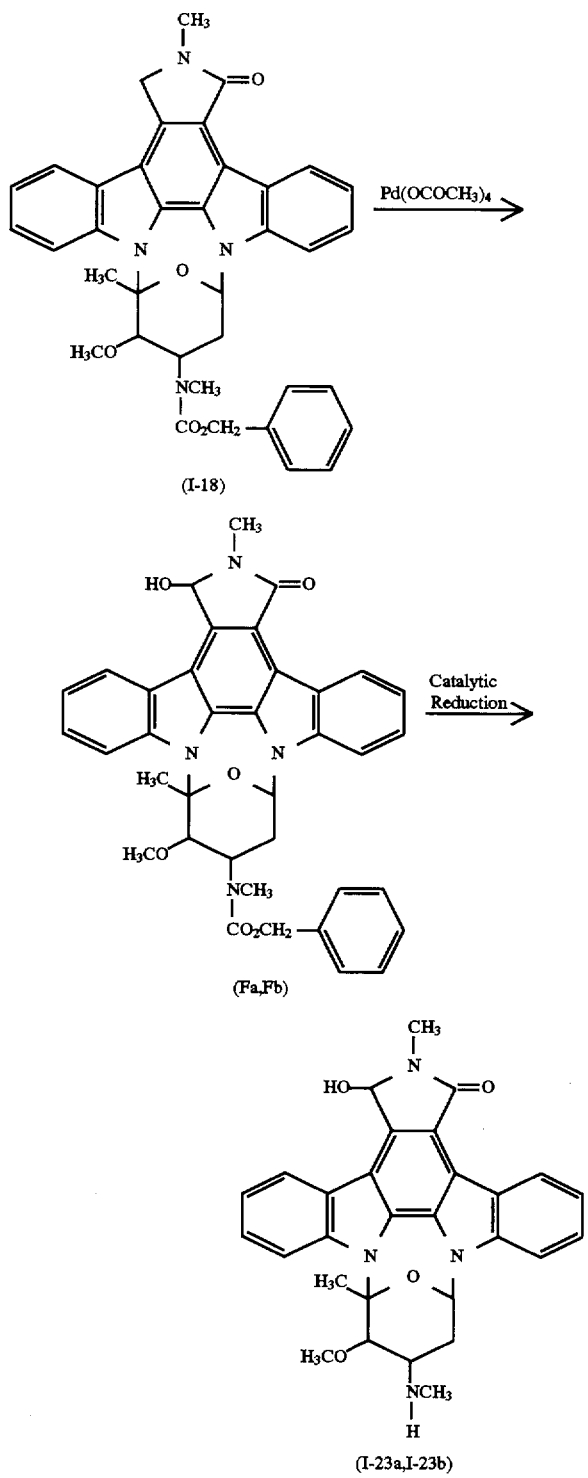

To a solution of 61.4 mg of Compound I-18 in 1.0 ml of acetic acid was added 46.3 mg of lead tetraacetate (purity: 95.6%), followed by stirring at room temperature for 3 hours. After about 30 ml of ethyl acetate was added, the reaction mixture was washed successively with water, a saturated aqueous solution of sodium carbonate, and a saturated aqueous solution of sodium chloride. The ethyl acetate layer was dried over sodium sulfate, followed by concentration under reduced pressure to dryness. The residue was purified by silica gel column chromatography [solvent system:toluene-ethyl acetate (8:1)] to give 24.0 mg of Compound (Fa) as the first eluted oxidation product and 25.4 mg of Compound (Fb) as the subsequently eluted oxidation product.

Oxidation product [Compound (Fa)];
$^1$H-NMR (400 MHz)(DMSO-$d_6$, 90° C.) δ; 9.28 (1H, ddd, J=0.7, 1.2, 7.8Hz), 8.46 (1H, ddd, J=0.7, 1.2, 7.8Hz), 7.87 (1H, d, J=8.5Hz), 7.58 (1H, d, J=8.3Hz), 7.2–7.5 (9H, m), 6.95 (1H, dd, J=5.9, 8.8Hz), 6.44 (1H, d, J=9.8Hz), 6.27 (1H, d, J=9.5Hz), 5.21 (2H), 4.68 (1H, ddd, J=2.5, 4.8, 12.4Hz), 4.23 (1H, br.s), 3.15 (3H, s), 2.75 (3H, s), 2.7–2.8 (1H, m), 2.65 (3H, s), 2.30 (3H, s), 2.2–2.4 (1H, m) Fab-MS (m/z): 630 (M)$^+$ Oxidation product [Compound (Fb)];
$^1$H-NMR (400 MHz) (DMSO-$d_6$, 90° C.) δ; 9.27 (1H, ddd, J=0.7, 1.2, 8.0Hz), 8.51 (1H, dt, J=7.3, 0.7Hz), 7.87 (1H, d, J=8.8Hz), 7.60 (1H, d, J=8.3Hz), 7.2–7.5 (9H, m), 6.95 (1H, dd, J=6.4, 8.5Hz), 6.44 (1H, d, J=9.8Hz), 6.26 (1H, d, J=9.5Hz), 5.21 (2H), 4.67 (1H, ddd, J=2.9, 4.0, 13.5Hz), 4.24 (1H, br.s), 3.15 (3H, s), 2.75 (3H, s), 2.7–2.8 (1H, m), 2.73 (3H, s), 2.29 (3H, s), 2.2–2.4 (1H, m) Fab-MS(m/z): 630 (M)$^+$ To a solution of 15.7 mg of the oxidation product [Compound (Fa)] in 1.0 ml of dimethylformamide was added 3 mg of 20% palladium hydroxide on activated carbon (Parrman catalyst), followed by stirring in hydrogen for 3 hours. After the catalyst was filtered off using celite, the reaction mixture was concentrated under reduced pressure, and the residue was purified by silica gel column chromatography (solvent system: 0.05% triethylamine-added chloroform-methanol (50:1)] to give 8.9 mg of Compound I-23a.

$^1$H-NMR (400 MHz)(DMSO-$d_6$) δ; 9.25 (1H, d, J=7.6Hz), 8.37 (1H, d, J=7.4Hz), 7.98 (1H, d, J=8.5Hz), 7.60 (1H, d, J=8.3Hz), 7.47 (1H, ddd, J=1.2, 7.1, 8.3Hz), 7.41 (1H, ddd, J=1.2, 7.1, 8.3Hz), 7.27 (2H, q, J=7.2Hz), 6.71 (1H, t, J=7.2Hz), 6.60 (1H, d, J=10.0Hz), 6.23 (1H, d, J=9.8Hz), 4.08 (1H, d, J=3.5Hz), 3.34 (3H, s), 3.14 (3H, s), 2.30 (3H, s), 1.46 (3H, s) Fab-MS (m/z): 497 (M+H)$^+$ By the same procedure as in the preparation of Compound I-23a, 8.9 mg of Compound I-23b was obtained from 12.7 mg of the oxidation product [Compound (Fb)].

$^1$H-NMR (400 MHz)(DMSO-$d_6$) δ; 9.26 (1H, d, J=7.8Hz), 8.42 (1H, dd, J=1.0, 7.8Hz), 7.97 (1H, d, J=8.5Hz), 7.60 (1H, d, J=8.3Hz), 7.47 (1H, ddd, J=1.2, 7.1, 8.3Hz), 7.41 (1H, ddd, J=1.2, 7.1, 8.3Hz), 7.27 (2H, m), 6.69 (1H, t, J=3.7Hz), 6.65 (1H, d, J=9.5Hz), 6.25 (1H, d, J=9.5Hz), 4.08 (1H, d, J=3.5Hz), 3.36 (3H, s), 3.13 (3H, s), 2.30 (3H, s), 1.52 (3H, s) Fab-MS (m/z): 497 (M+H)$^+$

REFERENCE EXAMPLE 5: SYNTHESIS OF COMPOUND I-25

To a solution of 400 mg (0.86 mmol) of staurosporine (Compound I-17) in 15 ml of THF were added 0.12 ml of formaldehyde and 27.0 mg (0.43 mmol) of sodium cyanoborohydride. The mixture was adjusted to pH 5–6 with 3N hydrochloric acid, and then stirred for 5 hours. After being adjusted to pH 1–2 with 3N hydrochloric acid, the mixture was made basic with 3N sodium hydroxide and extracted with chloroform. The extract was washed with water, and then dried over sodium sulfate. The solvent was evaporated, and the residue was purified by silica gel column chromatography (methanol/chloroform=1/20) to give 142.9 mg (yield 35%) of Compound I-25.

¹H-NMR (400 MHz, CDCl₃) δ; 9.445 (d, 1H, J=8.0Hz), 7.934 (d, 1H, J=7.1Hz), 7.860 (d, 1H, J=8.3Hz), 7.516-7.280 (m, 5H), 6.674 (m, 1H), 6.228 (br. s, 1H), 5.020 (s, 1H), 3.992 (br. s, 1H), 2.761 (s, 3H), 2.423 (s, 3H), 1.971 (br. s, 6H) Fab-MS (m/z); 481 (M+1)⁺

REFERENCE EXAMPLE 6: SYNTHESIS OF COMPOUND I-26

To a solution of 50 mg (0.11 mmol) of staurosporine (Compound I-17) in 2 ml of THF were added 0.04 ml of propionaldehyde and 10.9 mg (0.17 mmol) of sodium cyanoborohydride. The mixture was adjusted to pH 5-6 with 3N hydrochloric acid, and then stirred for 3.5 hours. After 3N hydrochloric acid was added, the reaction mixture was made basic with 3N sodium hydroxide and extracted with chloroform. The extract was washed with water, and dried over sodium sulfate. The solvent was evaporated, and the residue was purified by silica gel column chromatography (methanol/chloroform=1/20) to give 43.3 mg (yield 43%) of Compound I-26.

¹H-NMR (500 MHz, DMSO-d₆) δ; 9.458 (d, 1H, J=7.9Hz), 7.953 (d, 1H, J=7.1Hz), 7.823 (d, 1H, J=8.5Hz), 7.515-7.274 (m, 5H), 6.705 (m, 1H), 6.165 (s, 1H), 5.038 (s, 2H), 3.963 (s, 1H), 3.221 (t, 1H, J=7.5Hz), 2.657 (m, 2H), 2.562 (s, 3H), 2.429 (s, 3H), 2.102 (s, 3H), 1.256 (m, 2H), 0.7074 (t, 3H, J=7.3Hz) Fab-MS (m/z); 509 (M+1)⁺

REFERENCE EXAMPLE 7: SYNTHESIS OF COMPOUND I-27

To a solution of 50 mg (0.11 mmol) of staurosporine (Compound I-17) in 2 ml of THF were added 0.06 ml of capronaldehyde and 10.9 mg (0.17 mmol) of sodium cyanoborohydride. The mixture was adjusted to pH 5-6 with 3N hydrochloric acid, and then stirred for 3.5 hours. After being adjusted to pH 1-2 with 3N hydrochloric acid, the mixture was made basic with 3N sodium hydroxide and extracted with chloroform. The extract was washed with water, and then dried over sodium sulfate. The solvent was evaporated, and the residue was purified by silica gel column chromatography (methanol/chloroform=1/20) to give 19.8 mg (yield 34%) of Compound I-27.

¹H-NMR (400 MHz, CDCl₃) δ; 9.461 (d, 1H, J=7.6Hz), 7.886 (d, 1H, J=7.0Hz), 7.808 (d, 1H, J=8.6Hz), 7.485-7.211 (m, 5H), 6.691 (br. s, 1H), 6.611 (t, 1H, J=5.9Hz), 4.964 (s, 2H), 3.934 (br. s, 1H), 3.185 (m, 1H), 2.602 (m, 2H), 2.545 (s, 3H), 2.399 (s, 3H), 2.032 (s, 3H), 1.561-0.871 (m, 8H), 0.827 (t, 3H, J=7.2Hz) Fab-MS (m/z); 551 (M+1)⁺

REFERENCE EXAMPLE 8: SYNTHESIS OF COMPOUND I-34

To a solution of 840 mg of Compound I-2 in 10 ml of chloroform was added 5 ml of 0.6N hydrochloric acid/ethyl acetate. The resulting precipitate was filtered off and recrystallized from methanol to give 613 mg of Compound I-34.

¹H-NMR (DMSO-d₆) δ; 2.112 (m, 1H), 2.285 (s, 3H), 2.678 (s, 3H), 4.033 (br. s, 1H), 4.508 (s, 1H), 5.087 (s, 2H), 6.941 (dd, 1H, J=3.2, 9.5Hz), 7.310-8.099 (m, 7H), 9.335 (d, 1H, J=7.9Hz)

REFERENCE EXAMPLE 9: SYNTHESIS OF COMPOUND I-38

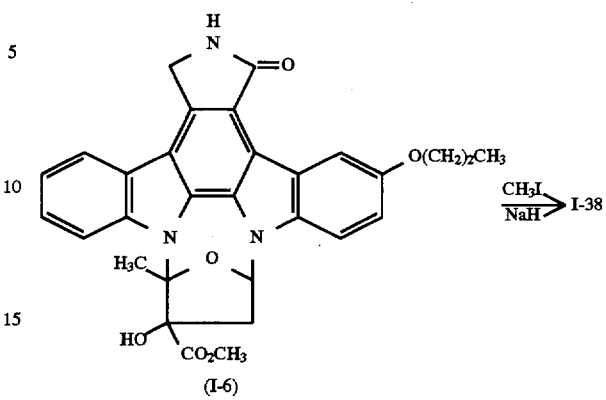

To a solution of 52.5 mg (0.1 mmol) of Compound I-6 in 2 ml of DMF was added 12 mg (0.3 mmol) of 60% sodium hydride under ice-cooling, followed by stirring for 15 minutes. Then, 19 μl (0.3 mmol) of methyl iodide was added to the solution, followed by stirring for 1.5 hours. The reaction mixture was diluted with ethyl acetate, washed with an aqueous solution of sodium chloride, and then dried over sodium sulfate. After the solvent was evaporated, the residue was purified by preparative TLC (methanol/chloroform=2/98) to give 23 mg of Compound I-38.

¹H-NMR (CDCl₃) δ; 1.109 (t, 3H, J=7.4Hz), 1.896 (m, 2H), 2.219 (s, 3H), 3.130 (s, 3H), 3.409 (s, 3H), 4.033 (s, 3H) 4.200 (t, 2H, J=6.5Hz), 4.960 (d, 1H, J=17.1Hz), 4.967 (d, 1H, J=17.1Hz), 6.924 (dd, 1H, J=5.3, 7.1Hz), 7.136-7.938 (m, 6H), 8.996 (d, 1H, J=2.4Hz) Fab-MS (m/z); 554 (M+1)⁺

REFERENCE EXAMPLE 10: SYNTHESIS OF COMPOUND I-40

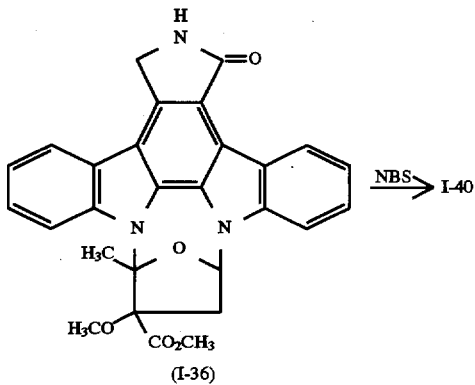

To a solution of 50 mg (0.1 mmol) of Compound I-36 in 1.5 ml of THF was added 53.4 mg (0.3 mmol) of N-bromosuccinimide at room temperature, followed by stirring for 2 hours. The mixture was diluted with chloroform, washed successively with a 5% aqueous solution of sodium thiosulfate, water, and an aqueous solution of sodium chloride, and then dried over sodium sulfate. After the solvent was evaporated, the residue was purified by preparative TLC (methanol/chloroform=2/98) to give 28 mg of Compound I-40.

¹H-NMR (CDCl₃) δ; 2.182 (s, 3H), 2.213 (dd, 1H, J=5.2, 13.5Hz), 3.152 (s, 3H), 3.400 (dd, 1H, J=7.4, 13.4Hz), 4.041

(s, 3H), 5.030 (d, 1H, J=16.7Hz), 5.072 (d, 1H, J=16.8Hz), 6.471 (br. s, 1H), 6.940 (d, 1H, J=5.3, 7.3Hz), 7.394–8.015 (m, 4H), 8.017 (d, 1H, J=1.9Hz), 9.478 (d, 1H, J=1.8Hz) Fab-MS (m/z); 640 (M+1)⁺

REFERENCE EXAMPLE 11: SYNTHESIS OF COMPOUND I-52

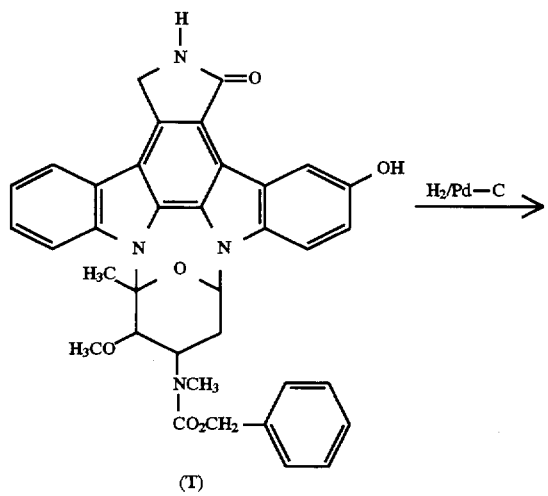

(T)

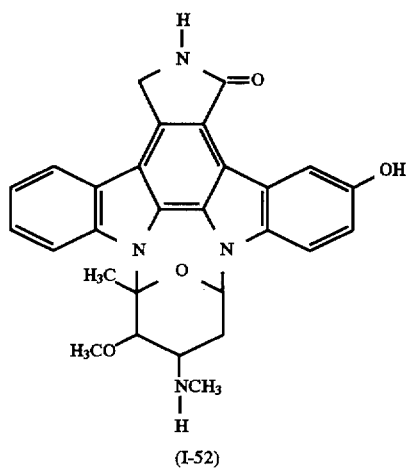

(I-52)

To a solution of 20 mg (0.032 mmol) of Compound (T) in 2 ml of DMF was added 20 mg of 10% Pd/C, followed by stirring in an atmosphere of hydrogen at room temperature for 2 days. After the completion of reaction, the mixture was filtered through celite, and the solvent was evaporated to give a crude product. The product was purified by silica gel column chromatography (methanol/chloroform=1/9) to give 4.7 mg (yield 30%) of Compound I-52.

¹H-NMR (400 MHz, DMSO-d₆) δ; 8.962 (s, 1H), 8.704 (s, 1H), 8.428 (s, 1H), 7.986-7.938 (m, 2H), 7.513-7.258 (m, 3H), 6.963 (dd, 1H, J=2.4, 8.6Hz), 6.635 (br. s, 1H), 4.917 (s, 2H), 4.647 (d, 1H, J=6.8Hz), 4.092 (br. s, 1H), 2.319 (s, 3H) Fab-MS (m/z); 483 (M+1)⁺

Industrial Applicability

According to the present invention, there are provided therapeutic agents for thrombocytopenia which are useful as medicines.

We claim:

1. A method of stimulating megakaryocyte production in a patient which comprises the steps of:

selecting a patient in need of increased megakaryocyte production; and administering to said patient an indolocarbazole derivative represented by the general formula (I):

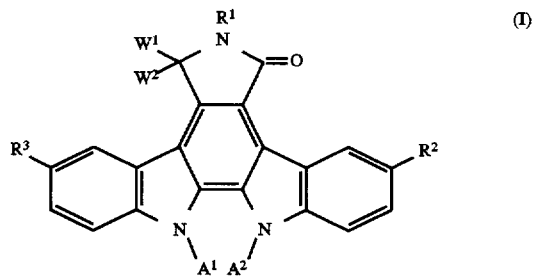

wherein $R^1$ represents hydrogen, lower alkyl, lower alkanoyl, benzyl or amino; $R^2$ represents hydrogen, hydroxy, lower alkoxy, lower alkanoyl, halogen or the formula (i):

$R^3$ represents hydrogen, lower alkanoyl, halogen, hydroxy or lower alkoxy; one of $W^1$ and $W^2$ is hydrogen, and the other is hydrogen, hydroxy or lower alkylthio, or $W^1$ and $W^2$ are combined together to represent oxygen; and $A^1$ and $A^2$ are the same and are hydrogen, or $A^1$ and $A^2$ are combined together to represent the formula (ii):

(wherein $R^6$ is hydrogen, benzyloxycarbonyl, lower alkyl or lower alkanoyl), or the formula (iii):

(wherein $R^4$ is hydrogen, lower alkyl, methoxymethyl or lower alkanoyl; and $R^5$ is hydrogen or lower alkoxycarbonyl), or a pharmaceutically acceptable salt thereof.

2. An indolocarbazole derivative represented by the general formula (II):

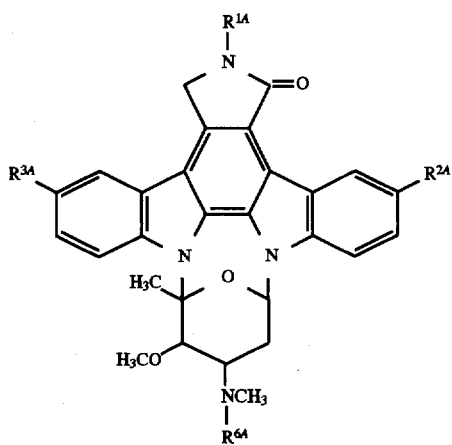

(II)

wherein (a) $R^{1A}$ is hydrogen or lower alkyl, $R^{3A}$ and $R^{6A}$ are hydrogen, and $R^{2A}$ is halogen or lower alkanoyl;

(b) $R^{1A}$ is hydrogen or lower alkyl, $R^{6A}$ is hydrogen, and $R^{2A}$ and $R^{3A}$ are lower alkanoyl;

(c) $R^{1A}$, $R^{3A}$ and $R^{6A}$ are hydrogen, and $R^{2A}$ is lower alkoxy;

or a pharmaceutically acceptable salt thereof.

3. A method according to claim 1, wherein $A^1$ and $A^2$ are combined together to represent said formula (ii).

* * * * *

UNITED STATES PATENT AND TRADEMARK OFFICE
CERTIFICATE OF CORRECTION

PATENT NO. : 5,674,867

DATED : October 7, 1997

INVENTOR(S): TATSUYA TAMAOKI ET AL.

It is certified that error appears in the above-identified patent and that said Letters Patent is hereby corrected as shown below:

<u>ON TITLE PAGE AT [54]</u> AND COL. 1, LINE 3, THE TITLE:

"MEGAKAICYOCYTE" should read --MEGAKARYOCYTE--.

<u>COLUMN 1</u>

Line 7, "1997." should read --1993.--

<u>COLUMN 8, TABLE 1</u>

Compound I-25, under table column headings $A^1$ $A^2$, "$\begin{array}{c} N-CH_3 \\ | \\ H \end{array}$"

should read --$\begin{array}{c} N-CH_3 \\ | \\ CH_3 \end{array}$--.

<u>COLUMN 9, TABLE 1</u>

Compound I-34, under table column heading $R^1$, "CH" should read --$CH_3$--.

<u>COLUMN 10, TABLE 1</u>

Compound I-36, under table column headings $A^1$ $A^2$, "HO—" should read --$H_3CO$— --.

UNITED STATES PATENT AND TRADEMARK OFFICE
CERTIFICATE OF CORRECTION

PATENT NO. : 5,674,867

DATED : October 7, 1997

INVENTOR(S): TATSUYA TAMAOKI ET AL.

It is certified that error appears in the above-identified patent and that said Letters Patent is hereby corrected as shown below:

COLUMN 12, TABLE 1

Compound I-38, under table column headings $A^1$ $A^2$, "HO—" should read --$H_3CO$— --.

COLUMN 12, TABLE 1

Compound I-40, under table column headings $A^1$ $A^2$, "HO—" should read --$H_3CO$— --.

COLUMN 14, TABLE 1

Compound I-49, under table column headings $A^1$ $A^2$, "$\begin{array}{c} N-CH_3 \\ | \\ H \end{array}$"

should read --$\begin{array}{c} N-CH_3 \\ | \\ CH_3 \end{array}$--.

COLUMN 14

Formula III, Line 55, "$H_2COCH_2O$—" should read --$H_3COCH_2O$— --.

COLUMN 15

Line 10, "$\xrightarrow{\text{Base}}_{R^{1a}}$" should read --$\xrightarrow{\text{Base}}_{R^{1a}X}$--.

UNITED STATES PATENT AND TRADEMARK OFFICE
CERTIFICATE OF CORRECTION

PATENT NO. : 5,674,867

DATED : October 7, 1997

INVENTOR(S): TATSUYA TAMAOKI ET AL.

It is certified that error appears in the above-identified patent and that said Letters Patent is hereby corrected as shown below:

COLUMN 24

Line 6, "compound" should read --Compound--.

COLUMN 27

Line 42, "added" should read --added to--.

COLUMN 35

Line 14, "$^1$-NMR" should read --$^1$H-NMR--.

COLUMN 36

Line 45, (R-1), "$(CH_3CO_2)_2O \longrightarrow$" should read --$(CH_3CO)_2O \longrightarrow$--.

Line 47, (R-2), "COOCH$_3$" should read --COCH$_3$--.

UNITED STATES PATENT AND TRADEMARK OFFICE
CERTIFICATE OF CORRECTION

PATENT NO. : 5,674,867

DATED : October 7, 1997

INVENTOR(S): TATSUYA TAMAOKI ET AL.

It is certified that error appears in the above-identified patent and that said Letters Patent is hereby corrected as shown below:

<u>COLUMN 40</u>

(R-5) "$\overset{|}{C}O_2CH-$" should read --$\overset{|}{C}O_2CH_2-$--.

Signed and Sealed this

Twenty-first Day of April, 1998

Attest:

BRUCE LEHMAN

Attesting Officer

Commissioner of Patents and Trademarks